(12) United States Patent
Lamonica et al.

(10) Patent No.: US 11,124,526 B2
(45) Date of Patent: Sep. 21, 2021

(54) CRYSTALLINE BETA-LACTAMASE INHIBITOR

(71) Applicant: Allecra Therapeutics SAS, Saint Louis (FR)

(72) Inventors: Alessandro Lamonica, Saint Louis (FR); Marco Forzatti, Monza (IT); Stefano Biondi, Pero (IT)

(73) Assignee: Allecra Therapeutics SAS, Saint Louis (FR)

( * ) Notice: Subject to any disclaimer, the term of this patent is extended or adjusted under 35 U.S.C. 154(b) by 0 days.

(21) Appl. No.: 16/177,406

(22) Filed: Oct. 31, 2018

(65) Prior Publication Data

US 2019/0071456 A1  Mar. 7, 2019

Related U.S. Application Data

(62) Division of application No. 15/035,176, filed as application No. PCT/EP2014/074108 on Nov. 7, 2014, now abandoned.

(30) Foreign Application Priority Data

Nov. 8, 2013 (GB) ...................................... 1319776
May 15, 2014 (GB) ...................................... 1408643

(51) Int. Cl.
*C07D 499/86* (2006.01)
*C07D 499/87* (2006.01)
*A61K 31/431* (2006.01)
*A61K 45/06* (2006.01)

(52) U.S. Cl.
CPC .......... *C07D 499/86* (2013.01); *A61K 31/431* (2013.01); *A61K 45/06* (2013.01); *C07D 499/87* (2013.01)

(58) Field of Classification Search
CPC .... A61K 31/431; A61K 45/06; C07D 499/86; C07D 499/87
USPC ................... 540/203, 302, 303, 309, 310
See application file for complete search history.

(56) References Cited

U.S. PATENT DOCUMENTS

| | | | |
|---|---|---|---|
| 4,562,073 A | 12/1985 | Micetich et al. | |
| 6,770,759 B2 | 8/2004 | Buynak et al. | |
| 7,687,488 B2 * | 3/2010 | Udayampalayam Palanisamy | C07D 499/86 514/192 |
| 9,963,465 B2 * | 5/2018 | Faini | C07D 499/87 |
| 10,201,532 B2 * | 2/2019 | Udayampalayam Palanisamy | C07D 499/883 |
| 2008/0015156 A1 * | 1/2008 | Udayampalayam Palanisamy | C07D 499/86 514/40 |
| 2009/0093423 A2 | 4/2009 | Udayampalayam Palanisamy et al. | |
| 2014/0057888 A1 * | 2/2014 | Udayampalayam Palanisamy | C07D 499/883 514/195 |
| 2015/0140059 A1 * | 5/2015 | Parhami | C07J 41/0055 424/423 |
| 2016/0159848 A1 * | 6/2016 | Harrington | C07J 9/00 552/610 |
| 2016/0159850 A1 * | 6/2016 | Parhami | A61P 19/00 424/93.7 |
| 2017/0101421 A1 * | 4/2017 | Faini | C07D 499/87 |

FOREIGN PATENT DOCUMENTS

WO   WO-2008010048 A2   1/2008
WO   WO-2012/070071 A1  5/2012

OTHER PUBLICATIONS

Tom Ellenberger( Biological Imaging by X-ray Diffraction Bio5325, X-Crystallography Lectures, 2006).*
International Search Report and Written Opinion for Application No. PCT/EP2014/074108 dated Dec. 12, 2014.
Lian Yu, "Amorphous pharmaceutical solids: preparation, characterization and stabilization", Advanced Drug Delivery Reviews, 48:27-42 (2001).
Fisher et al., Bacterial resistance to beta-lactam antibiotics: compelling opportunism, compelling opportunity, Chem. Rev., 105(2):395-424 (2005).
Shapiro, Speculative strategies for new antibacterials: all roads should not lead to Rome, J. Antibiot (Tokyo), 66(7):371-86 (2013).
Watkins et al., Novel β-lactamase inhibitors: a therapeutic hope against the scourge of multidrug resistance, Front Microbiol., 4:392 (2013).
Byrn et al., Pharmaceutical Solids: A Strategic Approach to Regulatory Considerations, Pharm. Res., 12(7):945-54 (1995).
Hirayama et al., Organic compound crystal preparation handbook principles and know-how, Maruzen Co., Ltd. (Jul. 25, 2008) pp. 17-23, 37-40, 45-51, and 57-65.
Japanese Patent Application No. 2016-527458, Notification of Reasons for Refusal, dated Oct. 25, 2018.
English translation of Office Action for corresponding Israel Application No. 245386, dated Jan. 30, 2020.

(Continued)

*Primary Examiner* — Joseph R Kosack
(74) *Attorney, Agent, or Firm* — Marshall, Gerstein & Borun LLP

(57) ABSTRACT

A crystalline compound of formula (I):

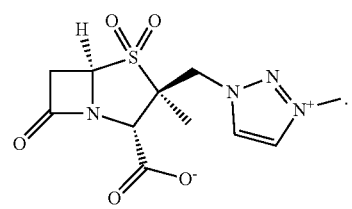

Formula (I)

The compound of formula (I) is a β-lactamase inhibitor and may be administered in combination with an antibacterial agent for prevention or treatment of bacterial infection.

18 Claims, 29 Drawing Sheets

(56) References Cited

OTHER PUBLICATIONS

Guillory, J. Keith. "Generation of Polymorphs, Hydrates, Solvates, and Amorphous Solids." H.G. Brittain (Ed.), *Polymorphism in Pharmaceutical Solids*, vol. 95. (Marcel Dekker, New York 1999): 183-226.
Grant, D. J.W. "Theory and Origin of Polymorphism." H.G. Brittain (Ed.), *Polymorphism in Pharmaceutical Solids*. (Marcel Dekker, New York 1999): 1-33 (pp. 1-10).
Office Action for corresponding European Patent Application No. EP 14 799 382.8-1110, dated Jan. 30, 2020.

* cited by examiner

CRYSTALLINE BETA-LACTAMASE INHIBITOR

CROSS-REFERENCE TO RELATED APPLICATION

This application is a divisional of U.S. patent application Ser. No. 15/035,176, filed May 6, 2016, which is the U.S. national phase of international application no. PCT/EP2014/074108, filed Nov. 7, 2014, which claims priority to Great Britain application No. 1408643.3, filed May 15, 2014 and Great Britain application No. 1319776.9, filed Nov. 8, 2013, the entire disclosures of which are hereby incorporated herein by reference.

FIELD OF THE INVENTION

The present invention relates to crystalline (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide, processes for the preparation thereof, pharmaceutical compositions comprising (2S,3S,5R)-3-methyl-3-((3-methyl-1H-1,2,3-triazol-3-ium-1-tl)methyl)-7-oxo-4-thia-1-azabicyclo[3.2.0]heptane-2-carboxylate 4,4-dioxide and uses of the compound, including uses of compositions containing the compound, in particular use with an antibacterial agent in treatment or prevention of bacterial infection.

BACKGROUND OF THE INVENTION

Emergence and dissemination of resistance is an inevitable consequence of the evolutionary dynamic set in motion by the introduction of antibiotics, irrespective of structural class or mode of action (Shapiro S. 2013. Speculative strategies for new antibacterials: all roads should not lead to Rome. J. Antibiot. 66: 371-386). Spread of resistance amongst clinically relevant pathogens has had an especially strong impact on the value of β-lactam antibiotics, heretofore regarded as very safe and efficacious therapies for serious bacterial infections. The appearance of new and aggressive β-lactamases, particularly extended spectrum β-lactamases (ESBLs) and other class A enzymes, has compromised the ability of β-lactams to combat infections, highlighting the need for development of new products (Fisher J F, Meroueh S O, Mobashery S. 2005. Bacterial resistance to β-lactam antibiotics: compelling opportunism, compelling opportunity. Chem. Rev. 105: 395-424). Whilst several β-lactamase inhibitors, which protect β-lactam antibiotics from hydrolysis, have been used in combination with some β-lactams, the capability of these β-lactamase inhibitors to preserve the antibacterial activity of β-lactams has eroded severely during the past decade, necessitating the search for new, more potent β-lactamase inhibitors to restore therapeutic utility of their β-lactam partners (Watkins R R, Papp-Wallace K M, Drawz S M, Bonomo R A. 2013. Novel β-lactamase inhibitors: a therapeutic hope against the scourge of multidrug resistance. Front. Microbiol. 4: 392).

WO 2008/010048 discloses the β-lactamase inhibitor (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (formula I):

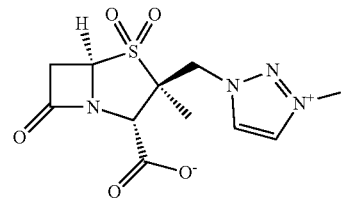

(Formula I)

WO 2008/010048 discloses formation of an amorphous compound of Formula (I) which is isolated by filtering and lyophilisation.

The present inventors have found that the compound of formula (I) as prepared by the process of WO 2008/010048 is hygroscopic, and has limited stability when stored at room temperature.

It is an object of the invention to provide a more stable form of the compound of formula (I).

It is a further object of the invention to provide a form of the compound of formula (I) that is easy to purify.

It is a further object of the invention to provide a form of the compound of formula (I) that is easy to handle.

SUMMARY OF THE INVENTION

The present inventors have developed crystalline compounds of formula (I). The present inventors have surprisingly found that crystalline compounds of formula (I) have improved thermal stability, are less hygroscopic and easier to purify and handle than the compound of formula (I) in amorphous form.

In a first aspect the invention provides a crystalline compound of formula (I):

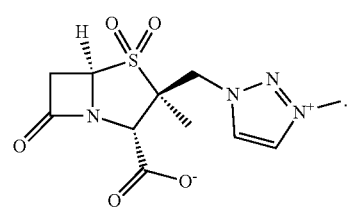

Formula (I)

In a first embodiment of the first aspect there is provided a crystalline compound of formula (I), hereinafter "Form A", characterised by an XRPD spectrum comprising four or more (preferably five or more, preferably six or more, preferably seven or more, preferably eight or more, preferably nine or more, preferably all ten) peaks selected from peaks with 2θ angles of: 8.82, 12.07, 14.43, 14.92, 16.26, 18.25, 19.06, 19.78, 20.82 and 23.51±0.1 degrees 2θ, optionally ±0.05 degrees 2θ.

Preferably, the XRPD spectrum of Form A has one, two, three, four or all five peaks selected from peaks with 2θ angles of: 8.82, 12.07, 14.43, 18.25 and 19.78±0.1 degrees 2θ.

Preferably, the XRPD spectrum of Form A has all ten peaks with 2θ angles of: 8.82, 12.07, 14.43, 14.92, 16.26, 18.25, 19.06, 19.78, 20.82 and 23.51±0.1 degrees 2θ, optionally ±0.05 degrees 2θ.

Preferably, Form A has a XRPD spectrum substantially as shown in FIG. 1.

Form A may be further characterised by its Thermo Gravimetric Analysis (TGA) curve showing an endothermic event at about 163° C.±2° C. The TGA curve may show a weight loss of about 6% up to 130° C.±2° C. due to water loss.

Preferably, Form A has a TGA curve substantially as shown in FIG. 9.

Form A may be further characterized by its differential scanning calorimetry (DSC) curve showing an endothermic event with a maximum at about 163° C.±2° C. The DSC curve may show an endothermic event starting at about 45° C.±2° C. due to water loss.

Preferably, Form A has a DSC curve substantially as shown in FIG. 5.

In a second embodiment of the first aspect there is provided a crystalline compound of formula (I), hereinafter "Form B", characterised by an XRPD spectrum comprising four or more (preferably five or more, preferably six or more, preferably seven or more, preferably eight or more, preferably nine or more, preferably all ten) peaks selected from peaks with 2θ angles of: 9.37, 10.34, 12.59, 13.17, 15.00, 15.63, 18.51, 19.10, 20.79, 23.93±0.1 degrees 2θ, optionally ±0.05 degrees 2θ.

Preferably, the XRPD spectrum of Form B has one, two, three, four or all five peaks selected from peaks with 2θ angles of: 10.34, 15.00, 15.63, 18.51 and 23.93±0.1 degrees 2θ.

Preferably, the XRPD spectrum of Form B has all ten peaks with 2θ angles of: 9.37, 10.34, 12.59, 13.17, 15.00, 15.63, 18.51, 19.10, 20.79 and 23.93±0.1 degrees 2θ, optionally ±0.05 degrees 2θ.

Preferably, Form B has a XRPD spectrum substantially as shown in FIG. 2.

Form B may be further characterised by its Thermo Gravimetric Analysis (TGA) curve showing an an endothermic event at about 155° C.±2° C.

The TGA curve may show a weight loss of about 8% up to 120° C.±2° C. correlated with water desorption.

Preferably, Form B has a TGA curve substantially as shown in FIG. 10.

Form B may be further characterized by its differential scanning calorimetry (DSC) curve showing an endothermic event with a maximum at about 180° C.±2° C. The DSC curve may show an endothermic event starting at about 50° C.±2° C. due to water loss.

Preferably, Form B has a DSC curve substantially as shown in FIG. 6.

In a third embodiment of the first aspect there is provided a crystalline compound of formula (I), hereinafter "Form C", characterised by an XRPD spectrum comprising four or more (preferably five or more, preferably six or more, preferably seven or more, preferably eight or more, preferably nine or more, preferably all ten) peaks selected from peaks with 2θ angles of: 9.33, 10.73, 14.85, 15.29, 15.77, 16.16, 18.60, 20.12, 21.00 and 23.22±0.1 degrees 2θ, optionally ±0.05 degrees 2θ.

Preferably, the XRPD spectrum of Form C has one, two, three, four or all five peaks selected from peaks with 2θ angles of: 10.73, 14.85, 15.29, 20.12 and 23.22±0.1 degrees 2θ.

Preferably, the XRPD spectrum of Form C has all ten peaks with 2θ angles of: 9.33, 10.73, 14.85, 15.29, 15.77, 16.16, 18.60, 20.12, 21.00 and 23.22±0.1 degrees 2θ, optionally ±0.05 degrees 2θ.

Preferably, Form C has a XRPD spectrum substantially as shown in FIG. 3 or FIG. 20.

Form C may be further characterised by its Thermo Gravimetric Analysis (TGA) curve showing an endothermic event at about 149° C.

The TGA curve may show a weight loss of about 3% up to 120° C.±2° C. correlated with water desorption.

Preferably, Form C has a TGA curve substantially as shown in FIG. 11.

Form C may be further characterized by its differential scanning calorimetry (DSC) curve showing an endothermic event with a maximum at about 185° C.±2° C.

Preferably, Form C has a DSC curve substantially as shown in FIG. 7.

In a fourth embodiment of the first aspect there is provided a crystalline compound of formula (I), hereinafter "Form D", characterised by an XRPD spectrum comprising four or more peaks (preferably five or more, preferably six or more, preferably seven or more, preferably eight or more, preferably nine or more, preferably all ten peaks) selected from peaks with 2θ angles of: 6.78, 15.45, 16.39, 17.10, 20.06, 20.63, 23.23, 23.68, 26.18 and 32.47±0.05 degrees 2θ.

Preferably, the XRPD spectrum of Form D has one, two, three, four or all five peaks selected from peaks with 2θ angles of: 6.78, 16.39, 17.10, 20.63 and 23.23, ±0.05 degrees 2θ.

Preferably, the XRPD spectrum of Form D has all ten peaks with 2θ angles of 6.78, 15.45, 16.39, 17.10, 20.06, 20.63, 23.23, 23.68, 26.18 and 32.47±0.05 degrees 2θ.

Preferably, Form D has an XRPD spectrum substantially as shown in FIG. 25.

In a fifth embodiment of the first aspect there is provided a crystalline compound of formula (I), hereinafter "Form E", characterised by an XRPD spectrum comprising four or more peaks (preferably five or more, preferably six or more, preferably seven or more, preferably eight or more, preferably nine or more, preferably all ten peaks) selected from peaks with 2θ angles of: 6.82, 15.04, 15.68, 16.47, 17.17, 18.44, 20.69, 23.34, 23.88 and 25.38±0.05 degrees 2θ.

Preferably, the XRPD spectrum of Form E has one, two, three, four or all five peaks selected from peaks with 2θ angles of: 15.04, 15.68, 16.47, 20.69 and 23.88±0.05 degrees 2θ.

Preferably, the XRPD spectrum of Form E has all ten peaks with 2θ angles of: 6.82, 15.04, 15.68, 16.47, 17.17, 18.44, 20.69, 23.34, 23.88 and 25.38±0.05 degrees 2θ.

Preferably, Form E has an XRPD spectrum substantially as shown in FIG. 27.

In a sixth embodiment of the first aspect there is provided a crystalline compound of formula (I), hereinafter "Form F", characterised by an XRPD spectrum comprising four or more peaks (preferably five or more, preferably six or more, preferably seven or more, preferably eight or more, preferably ten or more, preferably all eleven peaks) selected from peaks with 2θ angles of: 12.73, 15.36, 15.95, 16.42, 18.12, 20.48, 22.85, 23.22, 27.04, 27.69 and 32.47±0.05 degrees 2θ.

Preferably, the XRPD spectrum of Form F has one, two, three, four or all five peaks selected from peaks with 2θ angles of: 12.73, 15.36, 15.95, 16.42 and 20.48±0.5 degrees 2θ.

Preferably, the XRPD spectrum of Form F has all eleven peaks with 2θ angles of: 12.73, 15.36, 15.95, 16.42, 18.12, 20.48, 22.85, 23.22, 27.04, 27.69 and 32.47±0.05 degrees 2θ.

Preferably, Form F has an XRPD spectrum substantially as shown in FIG. 29.

In a second aspect the invention provides a process for preparing crystalline compound of formula (I):

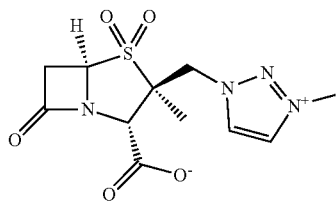

Formula (I)

the process comprising the steps of:

forming a formulation by dissolving or suspending an amorphous compound of formula (I) in a solvent or solvent mixture; and crystallising the compound of formula (I) from the formulation.

The amorphous compound of formula (I) in the formulation may substantially all be dissolved in the formulation; may substantially all be dispersed in the formulation; or may partly be dissolved and partly dispersed in the formulation.

The quantity of the amorphous compound of formula (I) used in the process of the second aspect of the invention may be below a solubility limit of the amorphous compound in the solvent or solvent mixture, in which case the formulation is a solution, or may be above the solubility limit, in which case the formulation is a suspension.

Solvents for dissolving the amorphous compound of formula (I) may be selected from solvents in which the amorphous compound of formula (I) has a solubility at 20° C. of greater than 200 mg/ml, optionally greater than 400 mg/ml. Solvents may be polar, protic or dipolar aprotic solvents. Exemplary polar, protic solvents are water; primary alcohols, preferably methanol, ethanol and 1-propanol. Further exemplary dipolar aprotic solvents are dimethylsulfoxide and N,N-dimethylformamide, N-methylpyrrolidone and the alike. Primary alcohols are preferred. Methanol and ethanol are particularly preferred. Water content of a primary alcohol solvent is preferably less than 4 wt %, more preferably less than 2 wt %. When the primary alcohol is methanol the water content is preferably less than 1%.

Crystallisation of a crystalline compound of formula (I) may be induced by adding an antisolvent to a formulation containing dissolved amorphous compound of formula (I). Antisolvents may be solvents in which the amorphous compound of formula (I) has a solubility at 20° C. of less than 50 mg/ml, optionally less than 30 mg/ml.

Antisolvents may be aprotic materials. Exemplary antisolvents are acetone, ethyl acetate, methyl-tert-butyl ether, heptane, 2-propanol, isopropyl acetate, diisopropyl ether, methylethyl ketone, tetrahydrofuran, anisole, and tert-butyl acetate.

In another embodiment of the second aspect, the amorphous compound of formula (I) may have little or no solubility in the solvent or solvent mixture used to form the formulation, in which case the formulation is a suspension.

A nucleating agent may be added to the formulation. The nucleating agent may be a crystalline seed of a compound of formula (I).

The purity of the solvent may affect solubility of the compound of formula (I) in the solvent, either in its amorphous form or in one or more of its crystalline forms.

The temperature of the formulation may be lowered following formation of the formulation. The solvent or solvent mixture may be heated during formation of the formulation, and may be cooled following formation of the formulation.

In a third aspect the invention provides crystalline compounds of formula (I) prepared by a process according to the second aspect of the invention.

The invention further provides crystalline compounds of formula (I) preparable by a process according to the second aspect of the invention.

For pharmaceuticals in which the active ingredient can exist in more than one polymorphic form, problems in dissolution and/or bioavailability of pharmaceutical compositions containing the compound can result if the manufacturing process leads to a polymorph with varying degrees of polymorphic purity and/or where the process does not control polymorphic interconversion.

If crystalline forms are made with polymorphic impurities, this may cause instability and it can accelerate significant interconversion to another polymorphic form. Therefore it is advantageous to produce crystalline forms with high polymorphic purity.

Preferably the crystalline compound of formula (I) according to the first or third aspects of the invention comprises more than 90% of a single crystalline polymorph of the compound, preferably more than 95%, more preferably more than 99%, even more preferably more than 99.5% and most preferably more than 99.8% as measured by XRPD or DSC, preferably as measured by XRPD. Preferably, the single polymorph is one of Form A, Form B, Form C, Form D, Form E, and Form F.

Preferably, the crystalline compound of formula (I) according to the first or third aspects of the present invention has a chemical purity of at least 95 wt %, more preferably at least 98%, more preferably at least 99%, more preferably at least 99.5%, even more preferably at least 99.8%, and most preferably at least 99.9%, preferably as measured by HPLC.

The crystalline compound of formula (I) may be suitable for reconstitution with a pharmaceutically acceptable vehicle for administration.

In a fourth aspect of the present invention there is provided a pharmaceutical composition comprising an antibiotic and the crystalline compound of formula (I) according to the first or third aspects of the present invention. Preferably, the pharmaceutical composition further comprises one or more pharmaceutically acceptable excipients.

In a fifth aspect the invention provides a pharmaceutical composition according to the fourth aspect for treatment of bacterial infection.

In a sixth aspect the invention provides a method of treating a bacterial infection comprising administering to a patient in need thereof a therapeutically effective amount of the pharmaceutical composition according to the fourth aspect of the present invention.

In a seventh aspect the invention provides a method of forming a pharmaceutical composition comprising a compound of formula (I), the method comprising the step of dissolving or dispersing the crystalline compound of formula (I) in a carrier liquid. Optionally the carrier liquid is a pharmaceutically acceptable vehicle for intravenous injections such as Dextrose, Sodium chloride & Dextrose 5 mixture, Sodium chloride, Sodium lactate, etc. Optionally, the carrier liquid is an aqueous saline solution.

The concentration of a compound of formula (I) in the pharmaceutical composition range from 1mg/ml to 700mg/ml, preferably from 100 to 500mg/ml, more preferably from 150 to 250 mg/ml.

DESCRIPTION OF THE DRAWINGS

The invention will now be described in more detail with reference to the Figures in which.

DETAILED DESCRIPTION OF THE INVENTION

Figure 1:
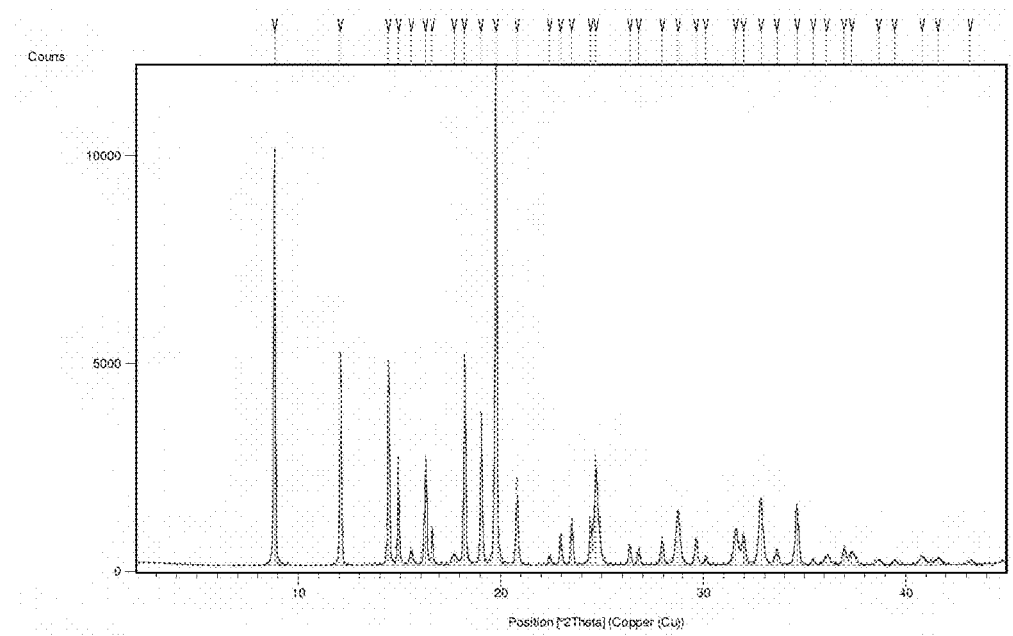
FIG. 1 is a X-ray powder diffraction pattern of Form A of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

The present invention provides crystalline (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide which is non-hygroscopic, thermally stable and has beneficial properties that avoid problems associated with the prior art forms.

The present invention further provides a process for forming crystalline (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide. The process allows formation of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide in high polymorphic purity.

Suitable crystallization techniques for forming crystalline compounds of formula (I) include, without limitation, precipitation and re-crystallization (including antisolvent crystallization) processes, with or without seeding with nucleating agents. In a preferred embodiment, antisolvent crystallization processes are used.

Diluted, saturated or super-saturated solutions may be used for crystallization.

A solution of an amorphous compound of formula (I) may be cooled to promote crystallization of crystalline compounds of formula (I).

An amorphous compound of formula (I) may be dissolved at a temperature in the range of 20-50° C. The solution may be cooled down to about 0° C. or about 10° C. to promote the crystallization.

Methods of preparing crystalline forms of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide, include, without limitation, the following methods:

Form A Method 1:
stirring a solution of amorphous compound of formula (I) in ethanol 96% at 20° C.,
collecting the solid by filtration.

Form A Method 2:
stirring a saturated solution of amorphous compound of formula (I) in ethanol 96% at 20° C.,
adding methyl tert-butyl ether as antisolvent,
stirring the mixture at room temperature overnight,
collecting the solid by filtration.

Form A Method 3:
stirring a saturated solution of amorphous compound of formula (I) in ethanol 96% at 20° C.,
seeding with nucleating agent,
adding heptane as antisolvent,
stirring the mixture at room temperature overnight,
collecting the solid by filtration.

Form A Method 4
stirring a saturated solution of amorphous compound of formula (I) in ethanol 96% at 20° C.,
seeding with nucleating agent,
adding 2-propanol as antisolvent,
stirring the mixture at room temperature overnight,
collecting the solid by filtration.

Form A Method 5
dissolving amorphous compound of formula (I) in ethanol 96% by heating to 35° C.
slowly adding (time: about 1 hour) methyl tert-butyl ether as antisolvent,
cooling the mixture to 10° C.
stirring the mixture at 10° C. overnight,
collecting the solid by filtration.

Form A Method 6
stirring a saturated solution of amorphous compound of formula (I) in ethanol 96% at 35° C.,
seeding the solution with nucleating agent,
slowly adding (time: about 20 min.) methyl tert-butyl ether as antisolvent at 20° C.,
cooling the mixture to 20° C. overnight,
collecting the solid by filtration Form A Method 7
stirring a saturated solution of amorphous compound of formula (I) in ethanol 96% at 40° C.,
seeding the solution with nucleating agent,
cooling the mixture to 20° C. over about 5 hours,
stirring the mixture at 20° C.,
collecting the solid by filtration Form B Method 1
stirring a saturated solution of amorphous compound of formula (I) in acetone at 40° C.,
collecting the solid by filtration.

Form C Method 1
stirring a solution of amorphous compound of formula (I) in ethanol 99.8% at 40° C.,
seeding the solution with nucleating agent at 36° C.
cooling the solution at 15° C.,
stirring the mixture overnight Forms D, E and F may be formed by crystallization from dimethylformamide solution. The present inventors have found that Forms D and E may crystallize initially from DMF solution but do not form once form F has formed.

Without wishing to be bound by any theory, this may be due to Form F having greater stability than either Form D or Form E.

Surprisingly, the present inventors have found that one crystal form of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide can be used to form another crystal form of this compound. One of crystal forms A, B and C may be used as a seed in crystallisation of another of forms A, B and C.

A pharmaceutical composition as described herein may be in an injectable form for intravenous injection. The composition may contain stabilizing agents. The composition may be in suitable sterile solid form ready for reconstitution to form an injectable solution.

A pharmaceutical composition containing a crystalline compound of formula (I) as described herein may be administered either alone or may be co-administered with therapeutically effective amount of an antibiotic.

A pharmaceutical composition as described herein may comprise an antibiotic and may comprise one or more conventional pharmaceutically acceptable excipient(s).

Exemplary antibiotics are □-lactam antibiotics, in particular penicillins and cephalosporins and may be selected from Amoxicillin, Ampicillin, Apalcillin, Azlocillin, Bacampicillin, Carbenacillin, Cloxacillin, Dicloxacillin, Flucloxacillin, Lenampicillin, Mecillinam, Methacillin, Mezlocillin, Nafcillin, Oxacillin, Penicillin G, Penicillin V, Piperacillin, Temocillin, Ticarcillin, Aztreonam, BAL30072, Carumonam, PTX2416, Tigemonam, Cefaclor, Cefadroxil, Cefalexin, Cefalotin, Cefamandole, Cefapirin, Cefazolin, Cefbuperazone, Cefdinir, Cefepime, Cefetamet, Cefixime, Cefmenoxime, Cefmetazole, Cefrninox, Cefonicid, Cefoperazone, Cefotaxime, Cefotetan, Cefotiam, Ceftiofur, Cefovecin, Cefoxtin, Cefpodoxime, Cefprozil, Cefquinome, Cefradine, Cefminox, Cefsulodin, Ceftaroline,Ceftazidime, Ceftezole, Ceftibuten, Ceftizoxime, Ceftobiprole, Ceftolozane, Ceftriaxone, Cefuroxime, Cefuzoname, Cephalexin, Cephalotin, Flomoxef, Latamoxef, Loracarbef Imipenem, Meropenem, Doripenem, Ertapenem, Biapenem, Panipenem, Faropenem or derivatives thereof.

The antibiotic may be selected from aminoglycosides: Amikacin, Arbekacin, Apramycin, Dibekacin, Gentamicin, Isepamicin, Kanamycin, Neomycin, Netilmicin, Plazomicin, Sisomicin, Spectinomyin, Streptomycin, Tobramycin or derivatives thereof.

The antibiotic may be selected from quinolones: Cinoxacin, Ciprofloxacin, Enofloxacin, Gatifloxacin, Gemifloxacin, Levofloxacin, Moxifloxacin, Nalidixic acid, Norfloxacin, Oxafloxacin, or derivatives thereof.

The antibiotic may be selected from antimicrobial peptides, for example Colistin, Polymyxin B or derivatives thereof.

A pharmaceutical composition as described herein may comprise only one or more than one antibiotic.

A pharmaceutical composition containing a crystalline compound of formula (I) may contain or be co-administered with bactericidal or permeability-increasing-g protein product (BPI) or efflux pump inhibitors to improve activity against gram negative bacteria and bacteria resistant to antimicrobial agents. Antiviral, antiparasitic, antifungal agents may also be administered in combination with the inhibitor compounds.

The pharmaceutical composition may contain complexing agents or anticoagulants, antioxidants, stabilizers, aminoglycosides, pharmaceutically acceptable salts or the like or mixtures thereof.

In particular the pharmaceutical composition may contain □-lactam antibiotics, preferably penicillins, cephalosporins, carbapenem, monobactams, more preferably piperacillin, cefepime; ceftriaxone; meropenem, aztreonam.

The pharmaceutical composition may contain buffers, for example sodium citrate, sodium acetate, sodium tartrate, sodium carbonate, sodium bicarbonate, morpholinopropanesulfonic acid, other phosphate buffers and the like and chelating agents like ethylenediaminetetraacetic acid (EDTA), diethylenetriaminepentaacetic acid, hydroxyethylenediaminetriacetic acid, nitrilotriacetic acid, 1,2-diaminocyclohexanetetraacetic acid, bis(2-aminoethyl)ethyleneglycoltetraacetic acid, 1,6-hexamethylenediaminetetraacetic acid and the like or pharmaceutically acceptable salts thereof.

A pharmaceutical composition as described herein may be administered to a human or warm-blooded animal by any suitable method, and preferably by intravenous injection.

EXAMPLES

All XRPD data described herein were acquired in transmission mode on an X'pert Pro instrument with X'celerator detector. The data were evaluated using the Highscore Plus software using copper as radiation source at a wavelength of 1.54 Å.

DSC analyses were run on a TA Q2000 MDSC instrument.

TGA analyses were run on a TA Q5000 instrument. The data were evaluated using Universal Analysis software.

Amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide, was prepared according to example 1 of WO 2008010048, the contents of which are incorporated herein by reference.

Example 1

Preparation of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide Form A Amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (200 mg) was dissolved in ethanol 96% (0.5 mL). The solution was stirred at 20° C., after 30 minutes a solid was formed. The mixture was stirred for 4 hours at 20° C. and the solid was isolated by filtration and dried overnight at room temperature in a vacuum oven. The obtained product (30 mg) was crystalline Form A which was characterized by an XRPD pattern as shown in FIG. 1 and summarized in Table 1.

| Angle [°2θ] | d-spacing [Å] |
| --- | --- |
| 8.8223 | 10.01516 |
| 12.0725 | 7.32517 |
| 14.4346 | 6.13137 |
| 14.9183 | 5.93364 |
| 16.2594 | 5.44711 |
| 18.2478 | 4.85778 |
| 19.0618 | 4.65213 |
| 19.7798 | 4.48485 |
| 20.8191 | 4.26326 |
| 23.5119 | 3.78074 |

Figure 5:
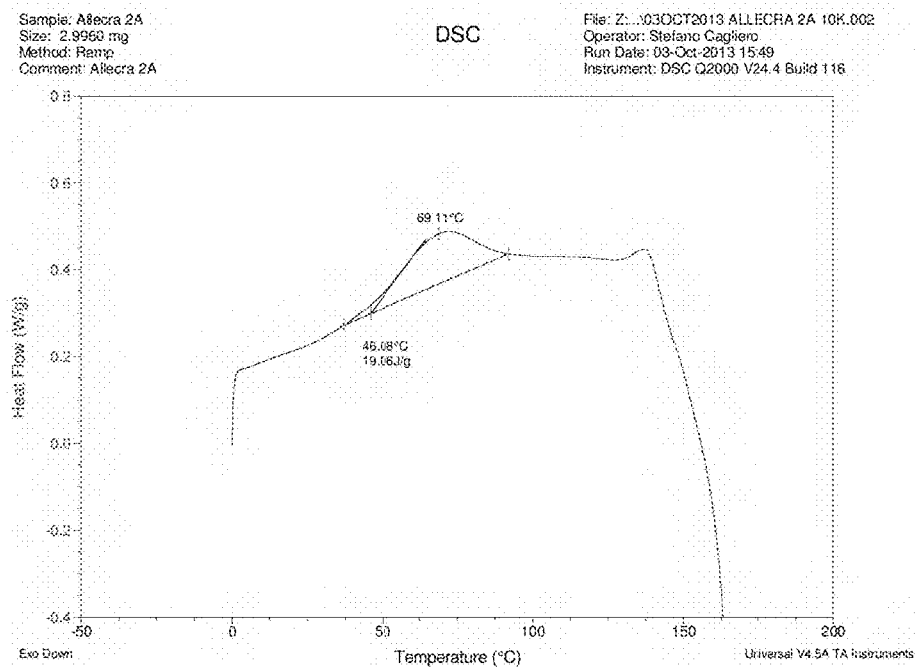
FIG. 5 is a differential scanning calorimetric thermogram of Form A of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.
Figure 9:
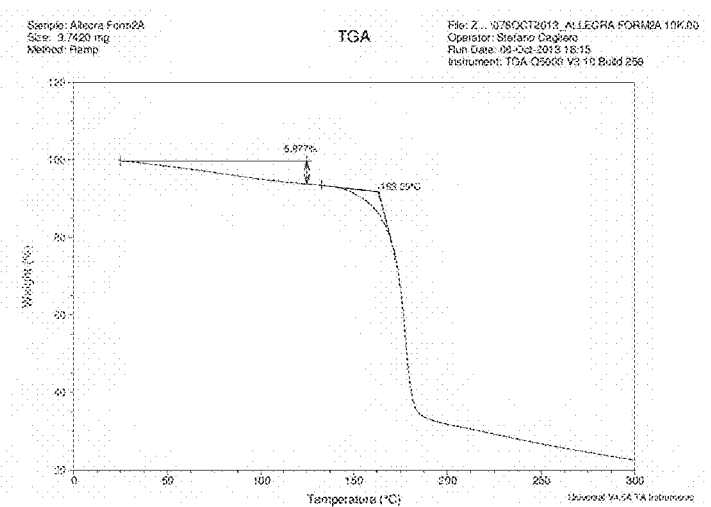
FIG. 9 is a thermogravimetric curve of Form A of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

DSC (FIG. 5) showed the sample to have a melting endotherm with a maximum at 163° C. TGA thermal curve is shown in FIG. 9.

Figure 13:
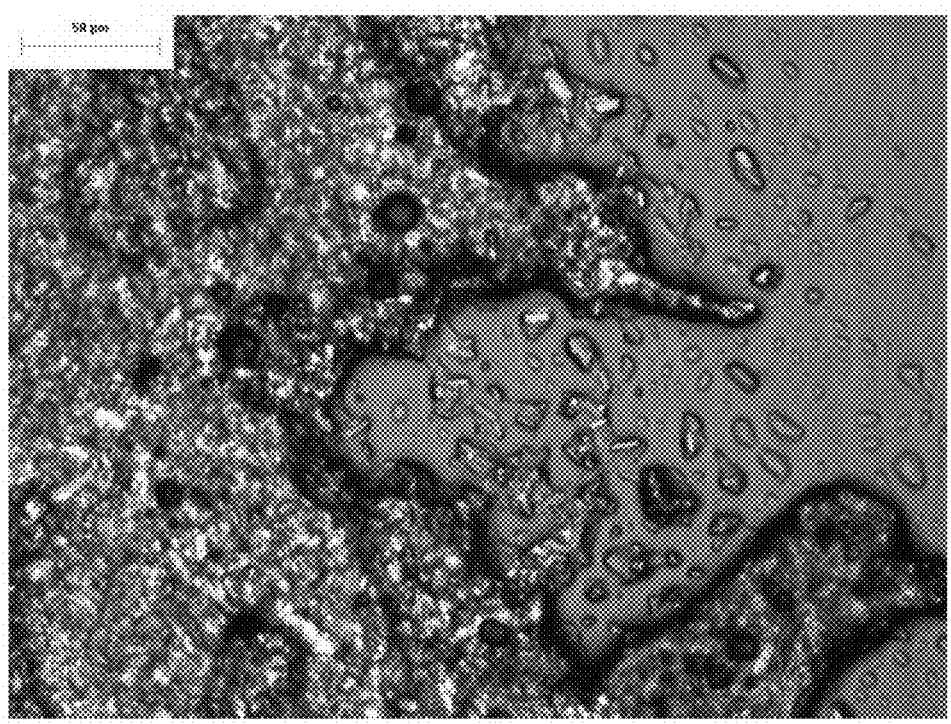
FIG. 13 is a 25× magnified optical microscope image of Form A of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

An optical microscope image of Form A is shown in FIG. 13.

Example 2

Preparation of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide Form A Amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (1 g) was suspended in ethanol 96% (3 mL). The resulting mixture was filtered through a syringe filter. The saturated solution was treated with methyl tert-butyl ether (0.5 mL) as antisolvent. The antisolvent addition results in a solid precipitation. The mixture was stirred at room temperature overnight and the solid was isolated by filtration and dried overnight at room temperature in a vacuum oven. The solid recovered was crystalline Form A characterized by XRPD concordant with XRPD pattern given in Example 1.

Example 3

Preparation of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide Form A Amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (1 g) was suspended in ethanol 96% (5 mL). The resulting mixture was filtered through a syringe filter. A pinch of Form A material was added to the solution as seed. The seed was not dissolved and the saturated solution was treated with heptane (0.5 mL) as antisolvent. The antisolvent addition results in a solid precipitation. The mixture was stirred at room temperature overnight and the solid was isolated by filtration and dried overnight at room temperature in a vacuum oven. The solid recovered was crystalline Form A characterized by XRPD concordant with XRPD pattern given in Example 1.

Example 4

Preparation of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide Form A Amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (1 g) was suspended in ethanol 96% (5 mL). The resulting mixture was filtered through a syringe filter. A pinch of Form A material was added to the solution as seed. The seed was not dissolved and the saturated solution was treated with 2-propanol (0.5 mL) as antisolvent. The antisolvent addition results in a solid precipitation. The mixture was stirred at room temperature overnight and the solid was isolated by filtration and dried overnight at room temperature in a vacuum oven. The solid recovered was crystalline Form A characterized by XRPD concordant with XRPD pattern given in Example 1.

Example 5

Preparation of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide Form A Amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (4 g) was weighed in a multimax vessel equipped with an impeller stirrer. The solid was suspended in ethanol 96% (32 mL). The mixture was heated to 35° C. and stirred at 800 RPM. At 35° C. the starting material seemed to be dissolved but the solution appeared slightly opaque. Methyl tert-butyl ether (8 mL) as antisolvent was added to the opaque solution over 1 hour. The addition of the antisolvent resulted in a solid formation. The mixture was cooled down to 10° C. over 1 hour. During the cooling ramp the material became sticky and the majority of the material adhered to the vessel walls. The mixture was stirred overnight and the solid obtained was discharged from the vessel by mechanical removal of the sticky solid from the vessel wall. The obtained mixture was filtered under vacuum; the cake was dried at room temperature in a vacuum oven for 60 hours to afford 2.75 g of a white solid. The solid recovered was crystalline Form A characterized by XRPD concordant with XRPD pattern given in Example 1.

Example 6

Preparation of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide Form A Amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (5 g) was weighed in a multimax vessel equipped with an impeller stirrer. The solid was suspended in ethanol 96% (30 mL). The mixture was heated to 35° C. and stirred at 800 RPM. At 35° C. the starting material seemed to be dissolved but the solution appeared slightly opaque. The opaque solution was filtered through a syringe filter to obtain a clear solution. A pinch of Form A material was added to the solution as seed; the seed was not dissolved and the mixture was cooled to 20° C. over 45 minutes. At this temperature methyl tert-butyl ether (10 mL) was added as antisolvent over 20 minutes. The addition of the antisolvent resulted in a sticky solid formation, the majority of the material adhered to the vessel walls. The mixture was stirred overnight and the solid obtained was discharged from the vessel by mechanical removal of the sticky solid from the vessel wall. The obtained mixture was filtered under vacuum; the cake was dried at room temperature in a vacuum oven for 60 hours to afford 3.61 g of a white solid. The solid recovered was crystalline Form A characterized by XRPD concordant with XRPD pattern given in Example 1.

Example 7

Preparation of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide Form A Amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (7 g) was weighed in a multimax vessel equipped with an impeller stirrer. The solid was suspended in ethanol 96% (21 mL). The mixture was heated to 40° C. and stirred at 400 RPM. At 40° C. the starting material seemed to be dissolved but the solution appeared slightly opaque. The opaque solution was filtered through a syringe filter to obtain a clear solution. A pinch of Form A material was added to the solution as seed; the seed was not dissolved and the mixture was stirred at 40° C. for 1 hour. The mixture is then cooled to 10° C. over 5 hours and stirred for 60 hours. The obtained material adhered to the vessel walls and was discharged by mechanical removal of the sticky solid from the vessel wall. The obtained mixture was filtered under vacuum; the cake was dried at room temperature in a vacuum oven for 18 hours to afford 5.54 g of a white solid. The solid recovered was crystalline Form A characterized by XRPD concordant with XRPD pattern given in Example 1.

Example 8

Figure 2:
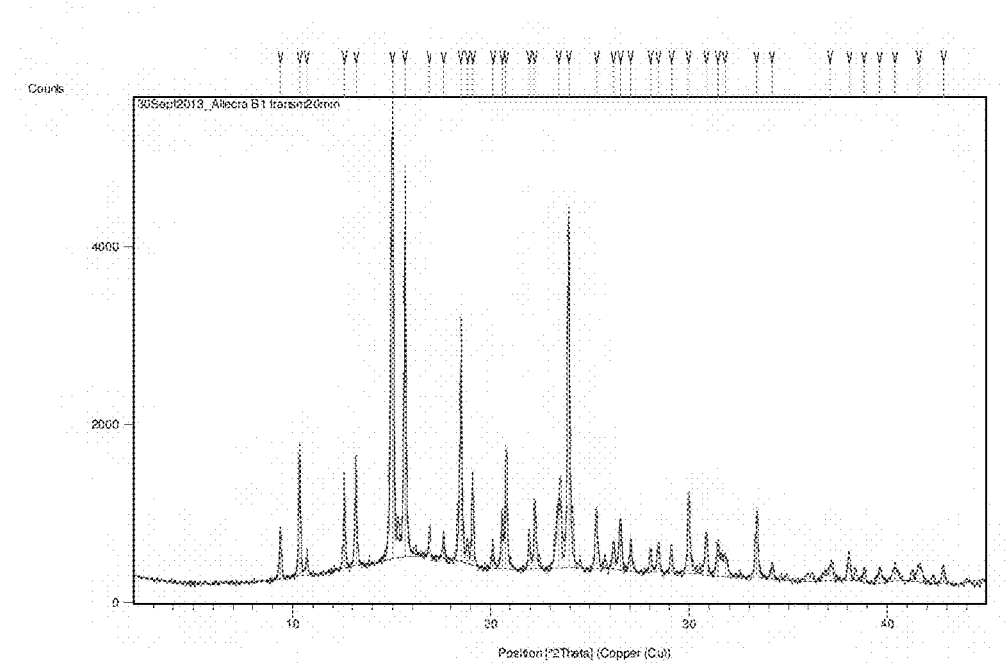
FIG. 2 is a X-ray powder diffraction pattern of Form B of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

Preparation of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide Form B Amorphous (2S,3S,5R)-3-methyl-3-((3-methyl-1H-1,2,3-triazol-3-ium-1-yl)methyl)-7-oxo-4-thia-1-azabicyclo [3.2.0]heptane-2-carboxylate 4,4-dioxide (200 mg) was suspended in acetone (0.5 mL) and the slurry was stirred for 4 hours at 40° C. The solid was isolated by filtration and dried overnight at room temperature in a vacuum oven. The obtained product (150 mg) was crystalline Form B which was characterized by an XRPD pattern as shown in FIG. 2 and summarized in Table 2.

| Angle [°2θ] | d-spacing [Å] |
| --- | --- |
| 9.3736 | 9.42739 |
| 10.343 | 8.54587 |
| 12.5922 | 7.024 |
| 13.172 | 6.71609 |
| 14.998 | 5.90227 |
| 15.636 | 5.66284 |
| 18.5083 | 4.79001 |
| 19.1049 | 4.64175 |
| 20.7935 | 4.26845 |
| 23.9264 | 3.71616 |

Figure 6:
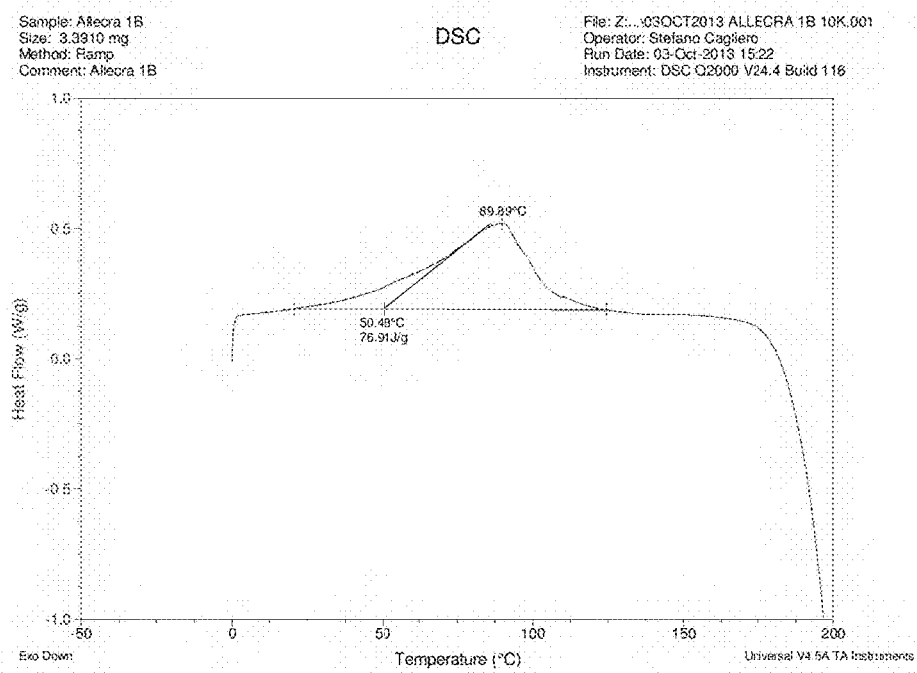
FIG. 6 is a differential scanning calorimetric thermogram of Form B of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.
Figure 10:
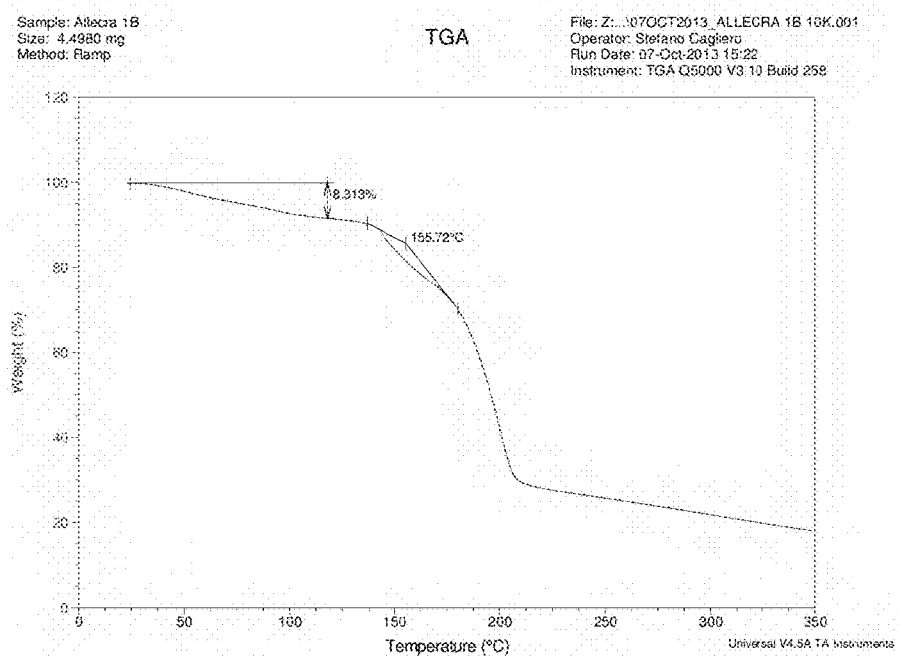
FIG. 10 is a thermogravimetric curve of Form B of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

DSC (FIG. 6) showed the sample to have a melting endotherm with a maximum at 180° C. TGA thermal curve is shown in FIG. 10.

Figure 14:
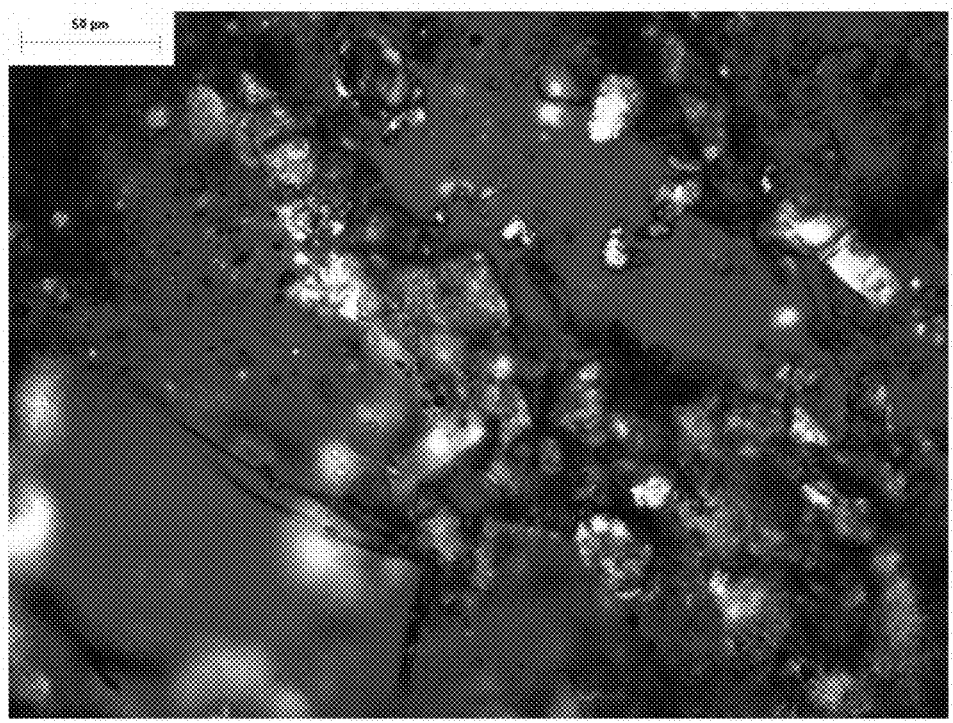
FIG. 14 is a 25× magnified optical microscope image of Form B of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

An optical microscope image of Form B is shown in FIG. 14.

Example 9

Figure 3:
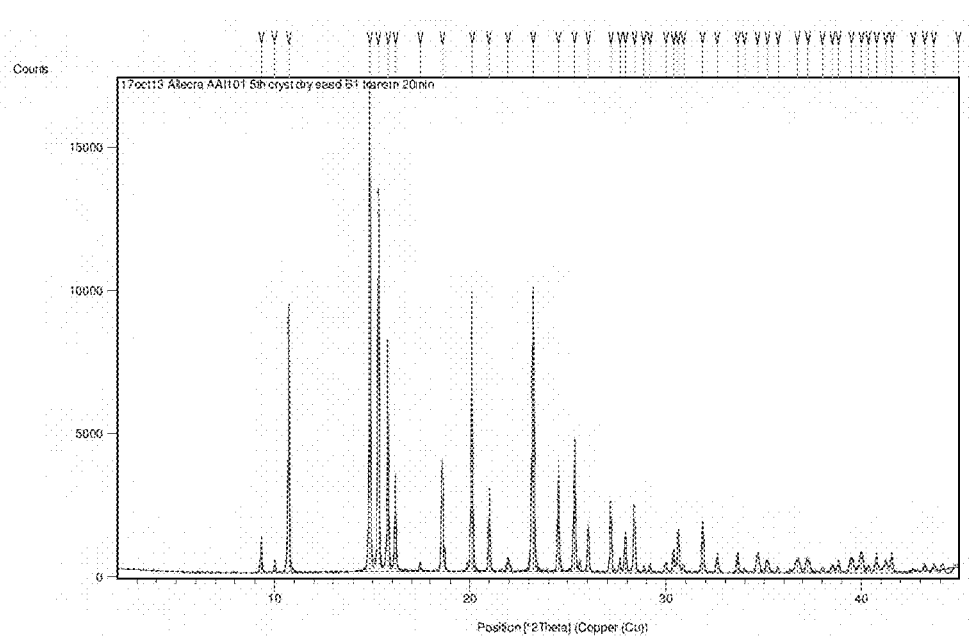
FIG. 3 is a X-ray powder diffraction pattern of Form C of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

Preparation of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide Form C Amorphous (2S,3S,5R)-3-methyl-3-((3-methyl-1H-1,2,3-triazol-3-ium-1-yl)methyl)-7-oxo-4-thia-1-azabicyclo [3.2.0]heptane-2-carboxylate 4,4-dioxide (5 g) was weighed in a multimax vessel equipped with an impeller stirrer. The solid was suspended in ethanol HPLC grade 99.8% (20 mL). The mixture was heated to 40° C. and stirred at 500 RPM. At 40° C. the starting material seemed to be dissolved but the solution appeared slightly opaque. The opaque solution was filtered through a syringe filter to obtain a clear solution. The solution was cooled to 36° C. over 15 minutes and Form B material (30 mg) was added to the solution as seed; the seed was not dissolved and promoted the product crystallization. The mixture was stirred at 36° C. for 30 minutes and is then cooled to 15° C. over 3.5 hours. The slurry was aged overnight and then was filtered under vacuum; the cake was dried at room temperature in a vacuum oven for 18 hours to afford 3.7 g of a white solid. The obtained product was crystalline Form C which was characterized by an XRPD pattern as shown in FIG. 3 and summarized in Table 3.

| Angle [°2θ] | d-spacing [Å] |
| --- | --- |
| 9.331 | 9.47026 |
| 10.7259 | 8.24161 |
| 14.8509 | 5.96039 |
| 15.2924 | 5.7893 |
| 15.7717 | 5.61443 |
| 16.1565 | 5.48158 |
| 18.6025 | 4.76595 |
| 20.1156 | 4.41074 |
| 20.9959 | 4.22776 |
| 23.2215 | 3.82734 |

Figure 7:
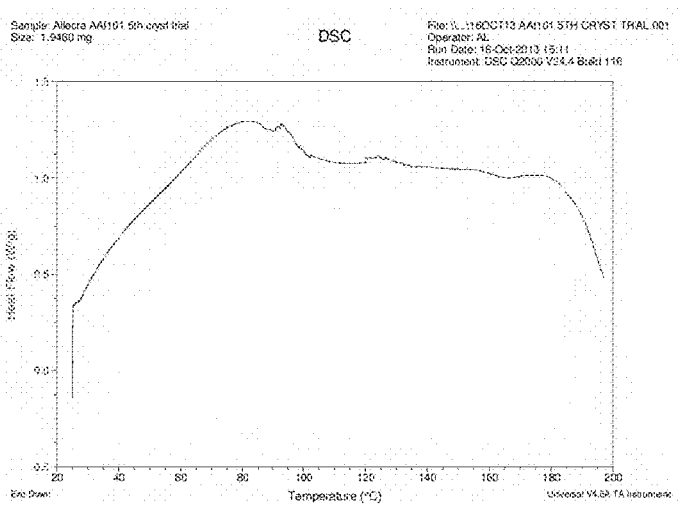
FIG. 7 is a differential scanning calorimetric thermogram of Form C of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.
Figure 8:
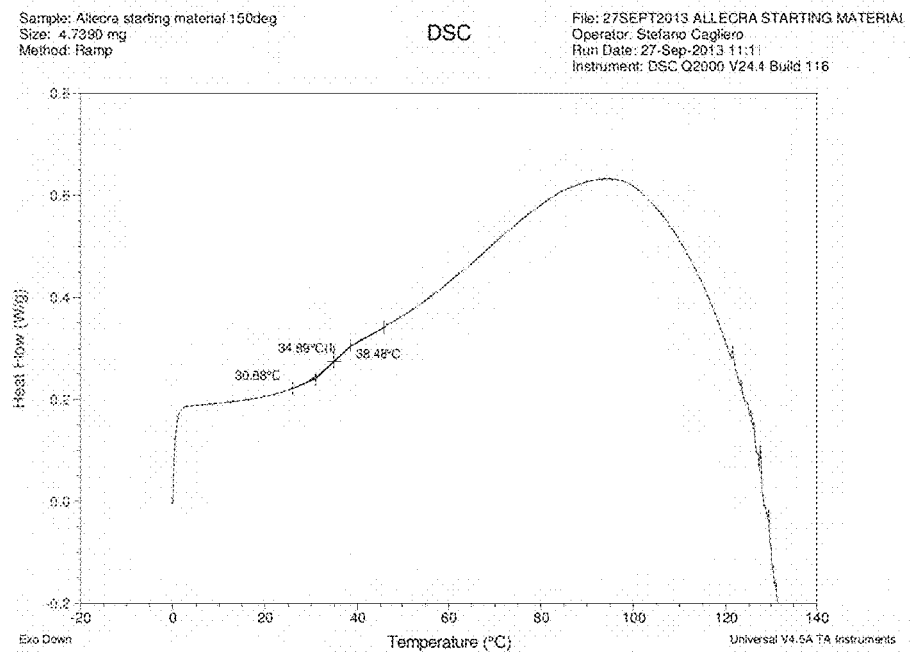
FIG. 8 is a differential scanning calorimetric thermogram of amorphous form of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

DSC (FIG. 7) showed the sample to have a melting endotherm with a maximum at 185° C.

Figure 11:
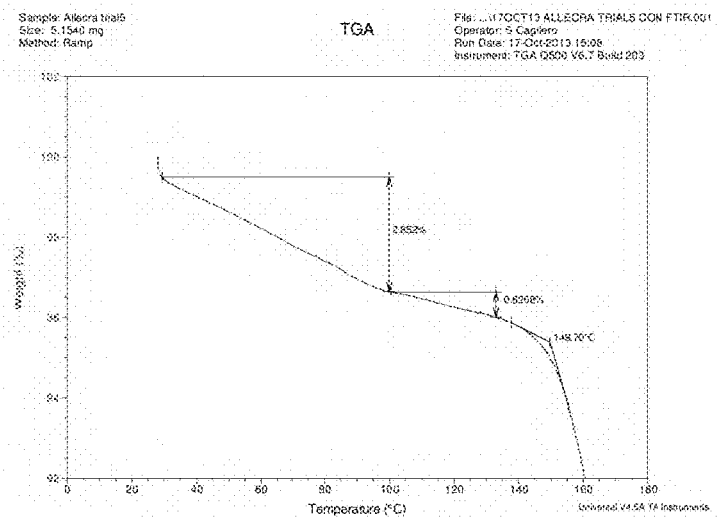
FIG. 11 is a thermogravimetric curve of Form C of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

TGA thermal curve is shown in FIG. 11.

Figure 15:
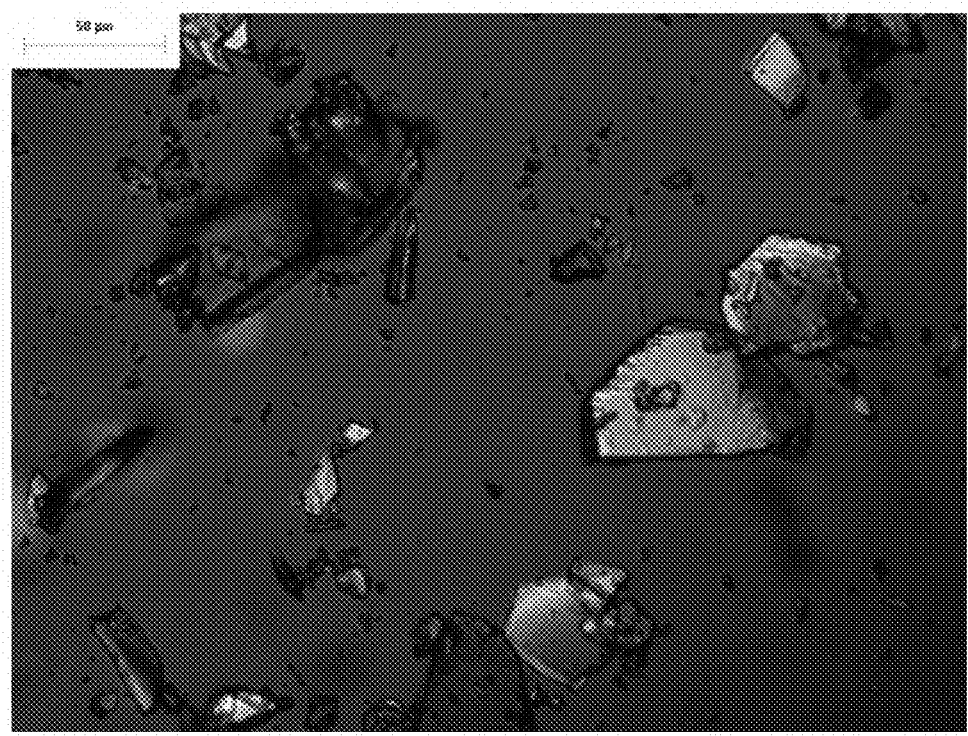
FIG. 15 is a 25× magnified optical microscope image of Form C of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

An optical microscope image of Form C is shown in FIG. 15.

Comparative Example

Figure 4:
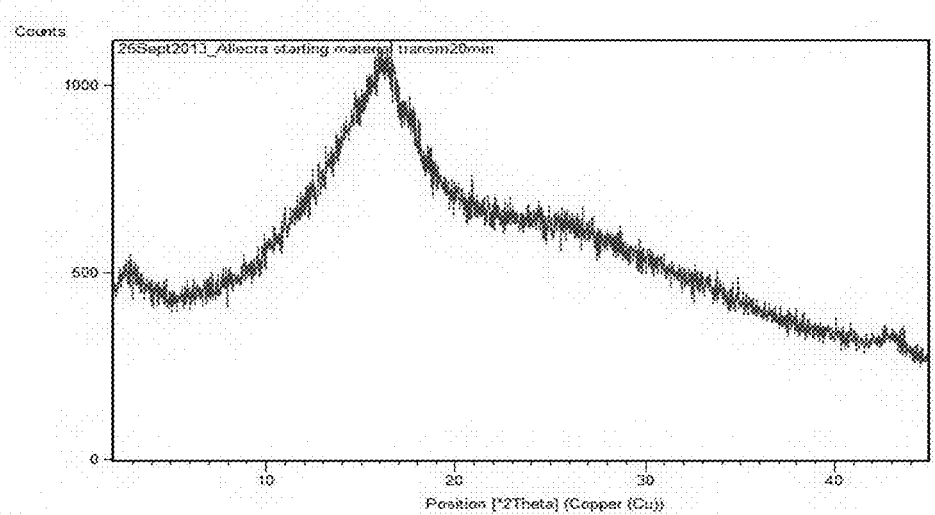
FIG. 4 is a X-ray powder diffraction pattern of amorphous form of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

The XRPD spectrum of amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide prepared as described in WO 2008/010048 is shown in FIG. 4. No crystalline character is detectable in this spectrum.

Solubility Evaluation

Figure 12:
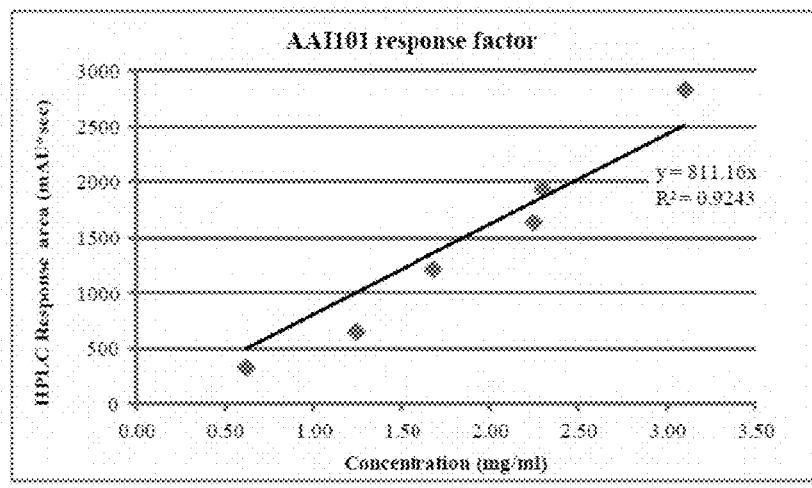
FIG. 12 is a plot of HPLC response area vs. concentration for solutions or suspensions of amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

Solubility values of solvents were calculated with respect to the HPLC response factor, set out in FIG. 12.

HPLC response factor was calculated for the amorphous compound of formula (I) using samples dissolved in acetonitrile/water 9/1 with the following method:

Column: ZORBAX Eclipse XDB-C18 (150×4.6 mm, 5 µm)

Temperature: 25° C.

Mobile phase: A: 0.05M Sodium ortophosphate/water, B: Acetonitrile

Gradient: from 5% of B to 95% of B in 10 min

Detector: UV λ=220 nm

| Sample | Concentration (mg/ml) | HPLC area |
| --- | --- | --- |
| 1 | 0.62 | 333.445 |
| 2 | 1.24 | 660.935 |
| 3 | 1.68 | 1219.92 |
| 4 | 2.25 | 1643.32 |
| 5 | 2.30 | 1940.44 |
| 6 | 3.10 | 2830.31 |

Slurries of the amorphous compound of formula (I) in the selected solvents were prepared and stirred at 20° C. and 40° C. for 4 hours.

Samples of each slurry were filtered and the mother liquors injected in HPLC.

The solid residual were isolated and analyzed by XRPD. The results are summarized in the following Table 4.

TABLE 4

Solubility of amorphous compound of formula (I)

| Solvent | Solubility (mg/ml) 20° C. | 40° C. |
|---|---|---|
| Acetone | 0 | 0 |
| Ethanol | 420 | >420 |
| Ethyl acetate | 0 | 0 |
| Methyl tert-butyl ether | 0 | 0 |
| Heptane | 0 | 0 |
| Water | >400 | >400 |
| 2-propanol | 23 | 28 |
| Iso-propyl acetate | 0 | 0 |
| Di-isopropyl ether | 0 | 0 |
| Methanol | >400 | >400 |
| Methylethyl ketone | 0 | 0 |
| Tetraydrofurane | 0 | 0 |
| Anisolo | 0 | 0 |
| Tert-butyl acetate | 0 | 0 |
| Dimethylsulfoxide | >400 | >400 |
| 1-propanol | 295 | >400 |
| 1-butanol | 97 | 167 |
| Acetonitrile | 6 | n.a. |
| Chlorobenzene | 0 | n.a. |
| Dichloromethane | 0 | n.a. |
| 1,4-dioxane | 0 | n.a. |
| Ethanol/methyl tert-butyl ether 20% | 52 | n.a. |
| Ethanol/methyl tert-butyl ether 40% | 16 | n.a. |
| Ethanol/acetone 20% | >300 | n.a. |
| Ethanol/acetone 40% | >300 | n.a. |

Form A characterization by Raman spectrum and Fourier transform infrared spectroscopy (FT-IR)

Figure 16:
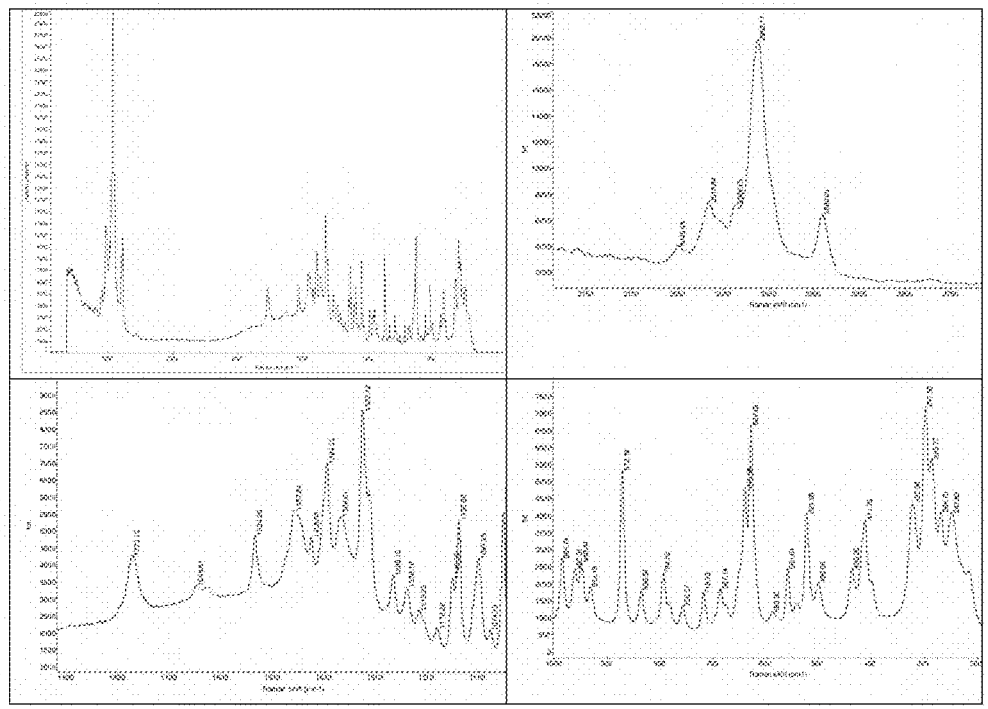
FIG. 16 is a Raman spectrum of Form A of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

The Raman spectrum of Form A is shown in FIG. 16 with the related peak bands list in Table 5.

Peak List:

| Position | Intensity |
|---|---|
| 247.89 | 4066.127 |
| 268.70 | 4076.600 |
| 285.77 | 5666.532 |
| 297.80 | 7186.507 |
| 322.04 | 4385.802 |
| 411.78 | 3861.458 |
| 436.26 | 2433.529 |
| 499.66 | 2023.949 |
| 521.68 | 4054.372 |
| 560.04 | 2419.952 |
| 588.92 | 1163.452 |
| 629.52 | 6647.466 |
| 640.58 | 4792.760 |
| 687.14 | 1836.374 |
| 718.78 | 1714.527 |
| 758.37 | 1345.186 |
| 794.58 | 2302.231 |
| 836.54 | 1806.043 |
| 872.19 | 5315.287 |
| 932.18 | 1889.917 |
| 949.44 | 2637.407 |
| 962.31 | 2419.830 |
| 985.74 | 2736.112 |
| 1049.63 | 5534.104 |
| 1074.79 | 2056.236 |
| 1097.28 | 4171.412 |
| 1135.89 | 5311.271 |
| 1148.59 | 3581.329 |
| 1178.28 | 2121.957 |
| 1215.25 | 2643.923 |
| 1239.16 | 3338.948 |
| 1266.18 | 3677.753 |
| 1325.12 | 8522.793 |
| 1368.61 | 5404.136 |
| 1394.52 | 6973.028 |
| 1425.05 | 4802.836 |
| 1457.84 | 5583.813 |
| 1534.20 | 4855.332 |
| 1648.81 | 3369.165 |
| 1773.12 | 4261.622 |
| 2890.60 | 6428.710 |
| 2962.11 | 19794.615 |
| 2986.55 | 7243.053 |
| 3015.84 | 7382.472 |
| 3049.43 | 4000.206 |

Figure 17:
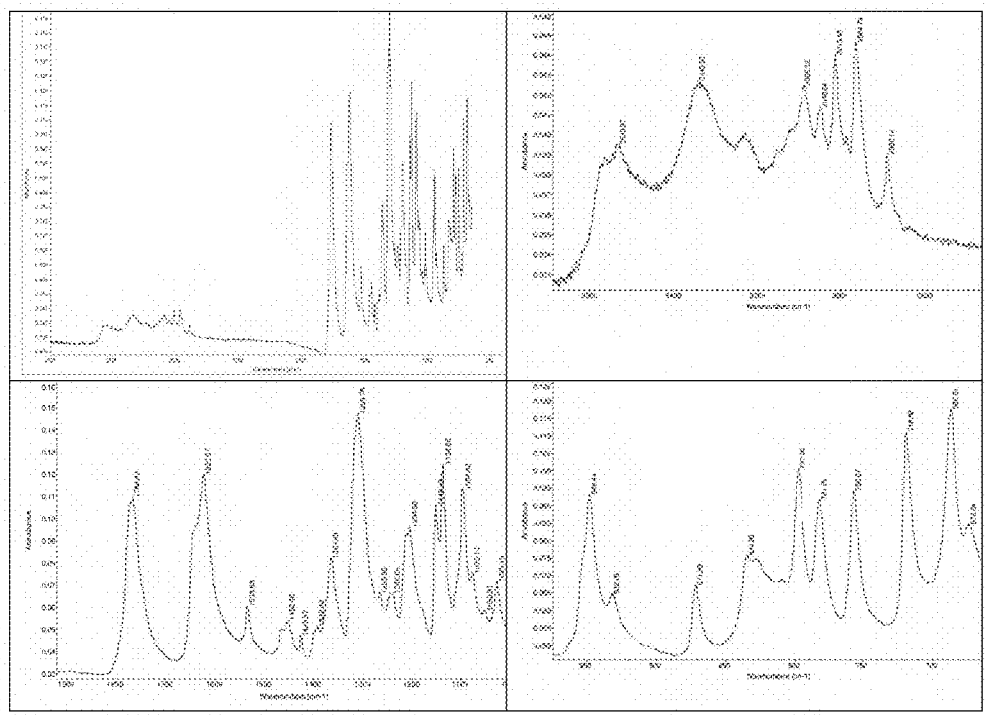
FIG. 17 is a FT-RT spectrum of Form A of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

FIG. 17 shows the FT-IR spectrum of Form A with the related peak bands list in Table 6.

Peak List

| Position | Intensity |
|---|---|
| 673.84 | 0.0846 |
| 686.51 | 0.118 |
| 718.98 | 0.111 |
| 756.67 | 0.0942 |
| 781.58 | 0.0916 |
| 797.38 | 0.100 |
| 834.89 | 0.0756 |
| 871.89 | 0.0672 |
| 932.05 | 0.0646 |
| 948.44 | 0.0932 |
| 1025.16 | 0.0712 |
| 1050.31 | 0.0580 |
| 1075.14 | 0.0752 |
| 1094.42 | 0.113 |
| 1134.65 | 0.124 |
| 1148.93 | 0.106 |
| 1204.60 | 0.0957 |
| 1240.06 | 0.0661 |
| 1235.85 | 0.0661 |
| 1309.76 | 0.147 |
| 1363.83 | 0.0819 |
| 1392.60 | 0.0512 |
| 1425.57 | 0.0468 |
| 1452.48 | 0.0538 |
| 1533.83 | 0.0601 |
| 1622.97 | 0.119 |
| 1766.49 | 0.109 |
| 2890.12 | 0.0390 |
| 2964.73 | 0.0446 |
| 3013.48 | 0.0440 |
| 3049.64 | 0.0414 |
| 3089.32 | 0.0425 |
| 3343.53 | 0.0427 |
| 3530.97 | 0.0395 |

Form C characterization by Raman spectrum and FT-IR

Figure 18:
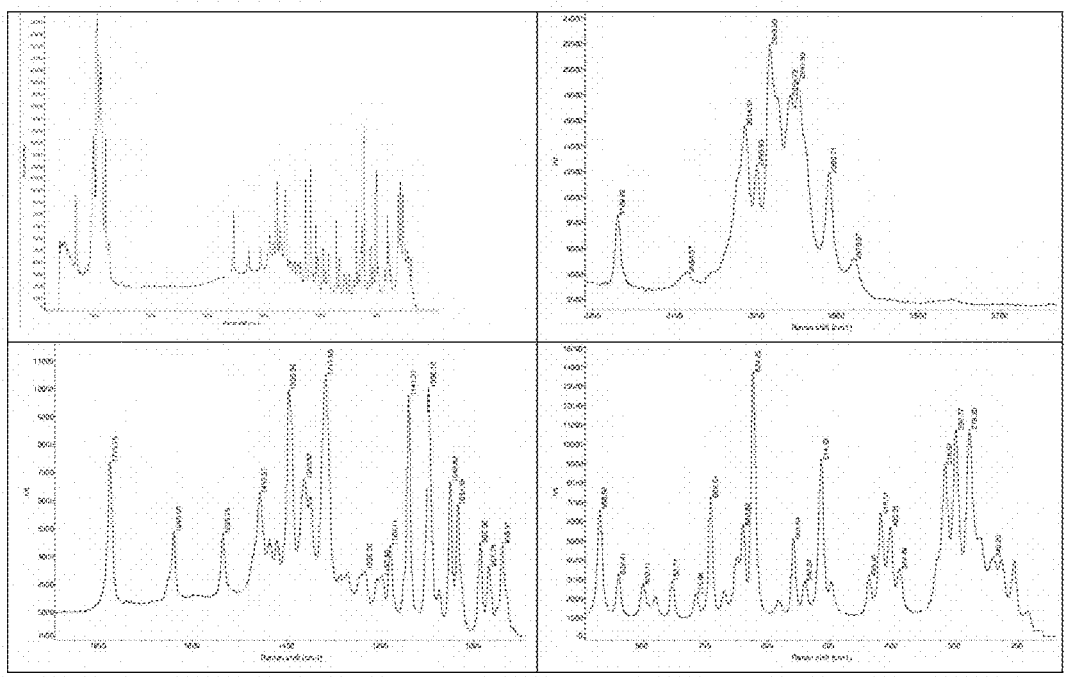
FIG. 18 is a Raman spectrum of Form C of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

The Raman spectrum of Form C is shown in FIG. 18 with the related peak bands list in Table 7.

Peak List:

| Position | Intensity |
|---|---|
| 240.20 | 4128.340 |
| 278.20 | 10739.558 |
| 299.77 | 10722.921 |
| 316.97 | 8908.874 |
| 389.49 | 3492.405 |
| 403.91 | 5676.352 |
| 419.31 | 6378.482 |
| 438.01 | 3159.695 |
| 514.23 | 9161.536 |
| 540.24 | 2881.736 |
| 560.59 | 5050.867 |
| 624.85 | 13700.852 |
| 640.80 | 5770.215 |
| 692.53 | 7222.112 |

-continued

| Position | Intensity |
|---|---|
| 715.48 | 2197.299 |
| 753.71 | 2920.133 |
| 800.11 | 2731.873 |
| 839.41 | 3232.516 |
| 868.99 | 6613.900 |
| 938.91 | 4443.281 |
| 967.79 | 3605.101 |
| 985.96 | 4480.407 |
| 1033.35 | 5823.568 |
| 1049.82 | 6638.105 |
| 1096.10 | 10022.146 |
| 1141.01 | 9717.918 |
| 1180.11 | 4361.805 |
| 1197.40 | 3267.057 |
| 1235.20 | 3502.896 |
| 1317.60 | 10464.665 |
| 1362.32 | 6745.435 |
| 1395.94 | 9937.875 |
| 1457.27 | 6235.580 |
| 1535.79 | 4771.901 |
| 1640.00 | 4841.217 |
| 1775.78 | 7336.955 |
| 2879.07 | 5109.468 |
| 2909.71 | 11865.885 |
| 2947.89 | 19208.596 |
| 2958.72 | 17883.816 |
| 2983.99 | 21848.400 |
| 2999.93 | 12395.464 |
| 3014.33 | 15550.745 |
| 3084.97 | 4124.013 |
| 3169.92 | 8548.841 |

Figure 19:
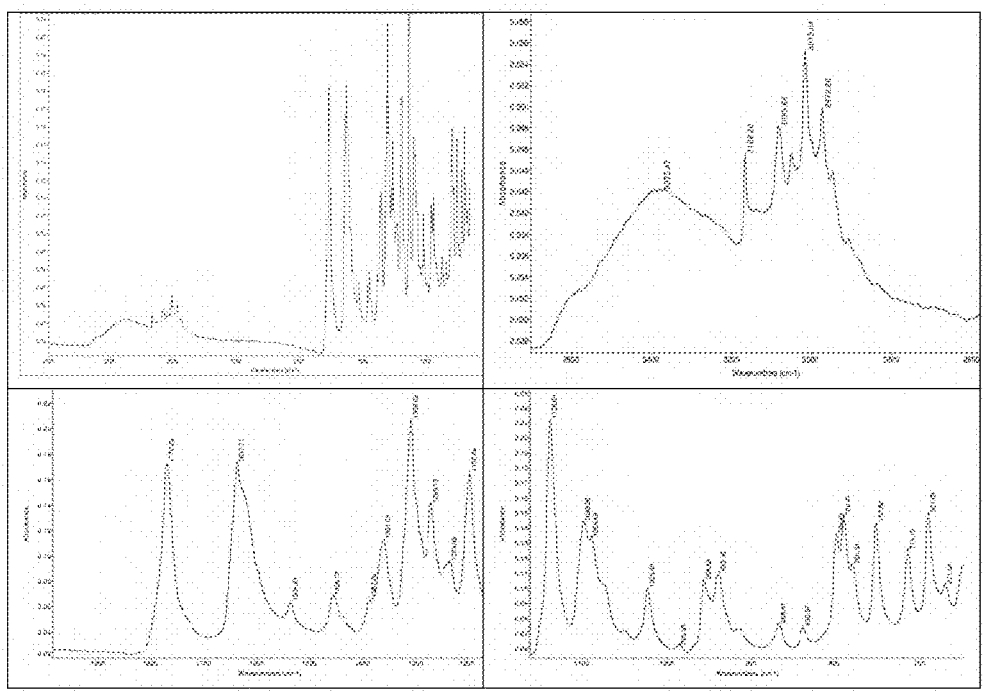
FIG. 19 is a FT-RT spectrum of Form C of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

The FT-IR spectrum of Form C is shown in FIG. 19 with the related peak bands list in Table 8.

Peak List:

| Position | Intensity |
|---|---|
| 671.04 | 0.103 |
| 691.08 | 0.151 |
| 715.10 | 0.126 |
| 752.68 | 0.145 |
| 780.33 | 0.117 |
| 790.47 | 0.149 |
| 799.40 | 0.136 |
| 838.87 | 0.0751 |
| 868.41 | 0.0772 |
| 939.45 | 0.111 |
| 956.58 | 0.106 |
| 985.83 | 0.0629 |
| 1023.40 | 0.101 |
| 1089.49 | 0.135 |
| 1098.28 | 0.145 |
| 1138.00 | 0.213 |
| 1195.45 | 0.166 |
| 1233.08 | 0.0960 |
| 1269.19 | 0.142 |
| 1309.02 | 0.208 |
| 1361.03 | 0.114 |
| 1387.96 | 0.0675 |
| 1456.72 | 0.0694 |
| 1536.21 | 0.0645 |
| 1637.71 | 0.174 |
| 1770.33 | 0.174 |
| 2972.20 | 0.0498 |
| 3015.04 | 0.0553 |
| 3083.68 | 0.0481 |
| 3168.20 | 0.0456 |
| 3375.47 | 0.0422 |

The analyses performed on Form A and Form C, including the information collected on the influence of the water content during the crystallization, has supported the hypothesis that Form A is a hydrate form with a rapid water exchange with the ambient and Form C is a more stable anhydrous form. Therefore, Form C was selected for further optimisation and scale-up of the crystallization process, and assessments as described below.

Optimization of Form C Crystallization

Example 10

Crystallization Procedure Using a Form C Seed

Preparation of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide Form C Amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (5 g) was weighed in a 50 ml multimax vessel equipped with an impeller stirrer. The solid was suspended in 20 ml of ethanol HPLC grade 99.8%. The mixture was heated to 40° C. and stirred at 700 RPM. At 40° C. the starting material was dissolved. The solution was cooled to 36° C. over 15 minutes and Form C material (27 mg) was added to the solution as seed; the seed was not dissolved and promoted the product crystallization. The mixture was cooled to 15° C. over 3.5 hours. The slurry was aged overnight and then was filtered under vacuum; the cake was dried at 30° C. in a vacuum oven for 40 hours to afford 3.7 g of a white solid. The solid showed an XRPD pattern for Form C.

The quality of the ethanol system was also investigated in the production of Form C material using 96% ethanol instead of ethanol HPLC grade 99.8% as described in Example 11.

Example 11

Preparation of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide Form A Amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (5 g) was weighed in a 50 ml multimax vessel equipped with an impeller stirrer. The solid was suspended in 20 ml of ethanol 96%. The mixture was heated to 40° C. and stirred at 700 RPM. At 40° C. the starting material seemed to be dissolved but the solution appeared slightly opaque. The opaque solution was filtered through a syringe filter to obtain a clear solution. The solution was cooled to 35° C. over 15 minutes and Form C material (28 mg) was added to the solution as seed. After 10 minutes at 35° C. was dissolved. The temperature was lowered to 30° C. over 15 minutes and more Form C material (27 mg) was added as seed. The seed was dissolved after 15 minutes. The solution was heated up to 35° C. and a pinch of Form B material was added to the solution but was dissolved after few minutes. A pinch of Form A material was added as seed; this time the seed did not dissolve and promoted the product crystallization. The mixture was cooled to 15° C. over 3.5 hours. The slurry was aged overnight and then was filtered under vacuum; the cake was dried at 30° C. in a vacuum oven for 18 hours to afford 3.1 g of a white solid. The solid showed an XRPD pattern concordant to Form A.

Examples 10 and 11 procedures demonstrate that the water content in the ethanol system can affect production of Forms A and C by a seeded approach. The formation of Form A material is possible in ethanol 96%, whereas the formation of Form C from a Form C crystal required use of ethanol HPLC grade 99.8%.

Example 12

Preparation of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide Form C Amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (8 g) was weighed in a 50 ml Multimax vessel equipped with an impeller stirrer. The solid was suspended in 20 ml of ethanol HPLC grade 99.8%. The mixture was heated to 40° C. and stirred at 800 RPM. At 40° C. the starting material was dissolved. The solution was cooled to 36° C. over 10 minutes and Form C material (24 mg) was added to the solution as seed; the seed was not dissolved and promoted the product crystallization. After 15 minutes stirring at 36° C. the mixture was cooled to 15° C. over 3.5 hours. The slurry was aged overnight and then was filtered under vacuum in nitrogen atmosphere (a funnel connected to a nitrogen flux was put over the filter). The cake was washed with 8 ml of ethanol HPLC grade 99.8%. The cake was dried inside the filter at 30° C. in a vacuum oven for 2 hours, after this time the product was transferred to a crystallizer and dried for further 16 hours. The product was analyzed by 1H-NMR to check the solvent content and showed the presence of ~1.3% w/w of ethanol. The cake was further dried at 35° C. in the vacuum oven for 6 hours. A new sample was taken and analyzed by 1H-NMR for solvent content. The ethanol residual was comparable to the first sample. The product was stored at −20° C. for the week-end and then put in the vacuum oven at 40° C. for 24 hours to yield 6 g of the product. The solid showed an XRPD pattern concordant with Form C. 1H-NMR confirmed the presence of ~1.3% w/w of ethanol residual in the cake.

The decrease of the seed loading did not have any negative impact on the product crystallization and was implemented in the scaled-up procedure as described in Example 13.

Example 13

Preparation scale up of (2S,3S,5R)-3-methyl-3-((3-methyl-1H-1,2,3-triazol-3-ium-1-yl)methyl)-7-oxo-4-thia-1-azabicyclo[3.2.0]heptane -2-carboxylate 4,4-dioxide Form C at 36 g scale.

Amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (36.45 g) was weighed in a 250 ml multimax vessel equipped with an impeller stirrer. The solid was suspended in 146 ml of ethanol HPLC grade 99.8%. The mixture was heated to 40° C. over 20 minutes. After 15 minutes at 40° C. the starting material was completely dissolved and the solution was cooled to 36° C. over 10 minutes and Form C material (110 mg) was added to the solution as seed; the seed was not dissolved and promoted the product crystallization. After 10 minutes stirring at 36° C. the mixture was cooled to 15° C. over 3.5 hours. The obtained mixture was aged overnight and then was filtered under vacuum. The cake was washed with 40 ml of ethanol HPLC grade 99.8% and three times with 40 ml of methyl tert-butyl ether to remove residual ethanol from the cake. The cake was deliquored in nitrogen atmosphere (a funnel connected to a nitrogen flux was put over the filter) under vacuum. The cake was dried in a vacuum oven for 24 hours to yield 26.8 g of the final product as a white solid.

The solid was analyzed by XRPD, TGA, optical microscopy (OM) and 1H-NMR.

Figure 20:
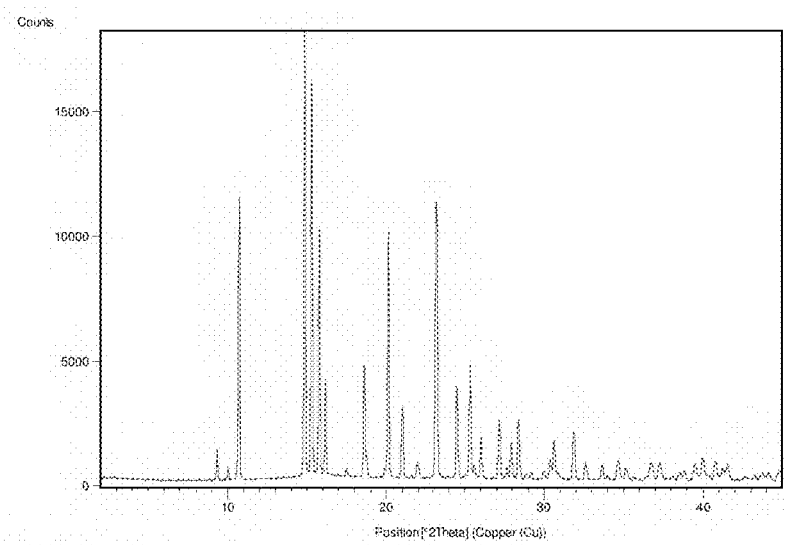
FIG. 20 is a X-ray powder diffraction pattern of Form C of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide, obtained according to Example 13.

The XRPD analysis of the product showed crystalline material with a pattern consistent with Form C (FIG. 20).

Figure 21:
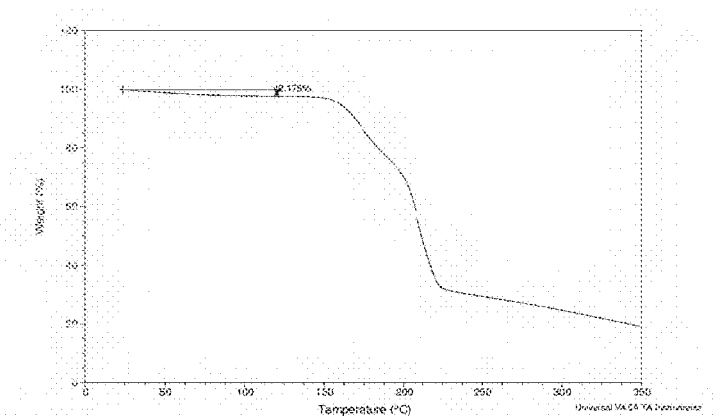
FIG. 21 is a thermogravimetric curve of Form C of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide, obtained according to Example 13.

The TGA analysis for the product (FIG. 21) shows a weight loss of circa 2% up to 120° C. probably due to adsorbed water and solvent residual.

Figure 22:
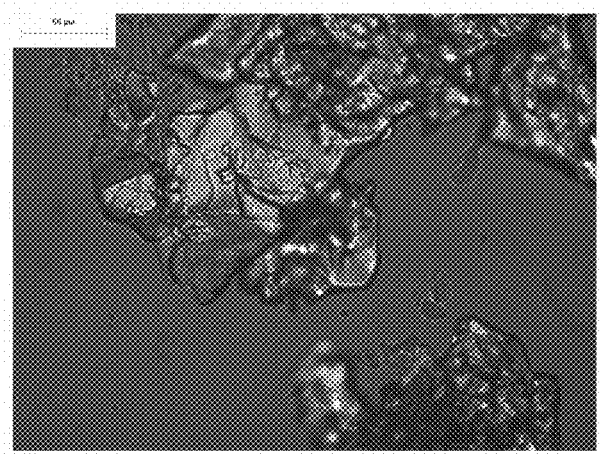
FIG. 22 is a 25× magnified optical microscope image of Form C of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide, obtained according to Example 13.

The OM analysis in FIG. 22 shows Form C crystals. Birifrangent particles using polarized light could be seen.

Figure 23:
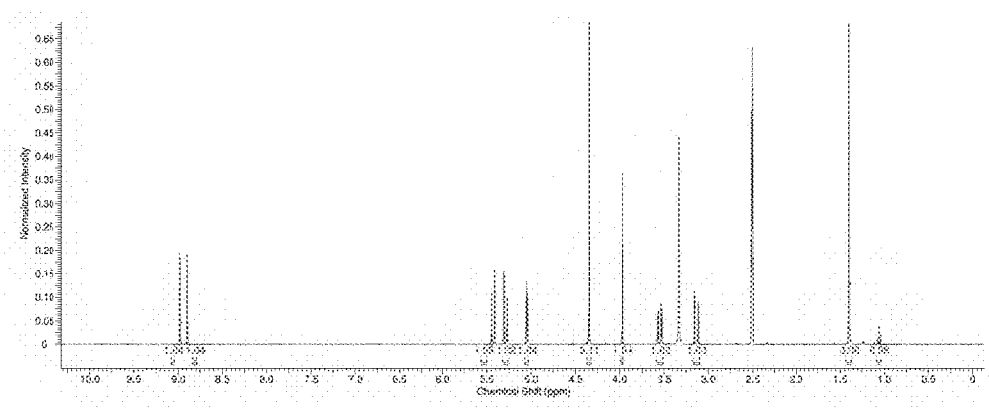
FIG. 23 is an 1H-NMR spectrum of Form C of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

The 1H-NMR spectrum (FIG. 23) is consistent with the structure of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide. The ethanol residue was calculated comparing the ethanol signal at 1.06 ppm and the API signal at 1.40 ppm. Considering integrals values, number of protons and the molecular weight of the reference signals the estimated ethanol residue is equal to 0.4% w/w respect to the API.

Solubility Assessment in Saline Physiological Solution

The Form C solubility was calculated by HPLC employing a dedicated walk-up method. The product obtained by the scaled up procedure described in Example 13 was used to perform the experiments.

1.9 g of the product was suspended in 1 ml of commercial physiologic solution (0.9% of NaCl) at ambient temperature (~20 ° C.). The suspension resulted slightly opaque and quite viscous after 30 min. After this time the suspension was sampled and the sample injected in HPLC to determine its concentration. After 2 hrs stirring the solid residue was completely dissolved. The addition of more solid was not performed to avoid the gelatinisation of the viscous solution. A sample was taken and injected in HPLC to determine its concentration. The solution was stirred other 3 hrs and sampled again. The 5 hrs sample was also injected in HPLC to determine its concentration. The HPLC traces did not show the formation of significant impurities. Table 9 shows the solubility results for the time-points selected.

| Physiological solution | Timepoint | Solubility (mg/ml) at ambient temperature |
|---|---|---|
| 1 | 30 mins | 772 |
| 2 | 2 hours | >883 |
| 3 | 5 hours | >812 |

Particle Size Distribution

Figure 24:
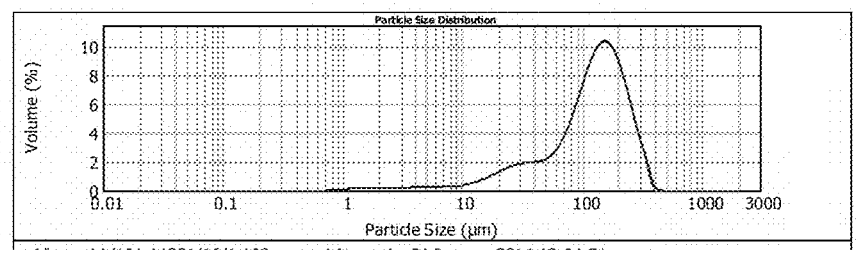
FIG. 24 shows particle size distribution curves of Form C of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide, obtained according to Example 13.
Figure 24:
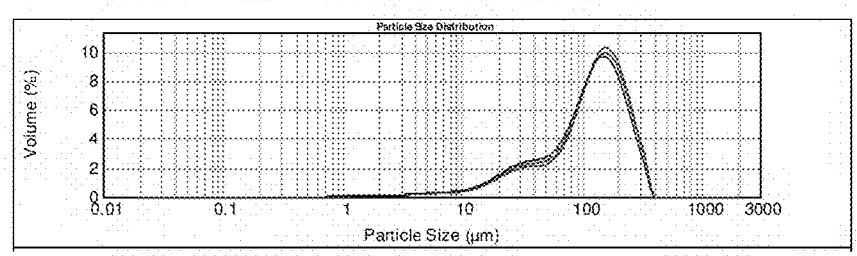
Figure 24:
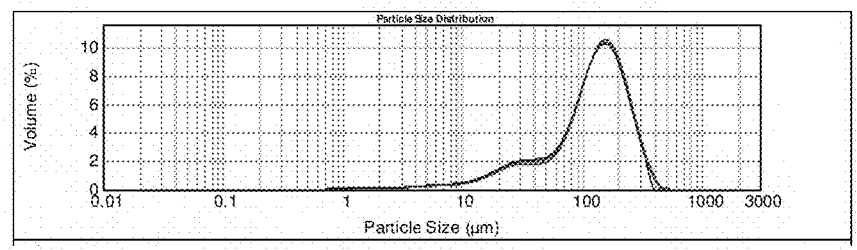

The particle size analysis was performed on the product obtained by the scaled up procedure described in Example 13 using the procedure described below. Three measurements for each suspension were recorded and the results are shown in FIG. 24 and in Table 10.

| Sample Name | d (0.1) | d (0.5) | d (0.9) |
|---|---|---|---|
| Suspension 1, Measurement 1 | 29.08 | 129.34 | 249.92 |
| Suspension 1, Measurement 2 | 28.94 | 128.69 | 246.31 |
| Suspension 1, Measurement 3 | 28.90 | 128.42 | 247.37 |
| Suspension 2, Measurement 1 | 28.26 | 130.37 | 251.74 |
| Suspension 2, Measurement 2 | 26.80 | 125.95 | 248.77 |
| Suspension 2, Measurement 3 | 25.40 | 119.25 | 239.11 |

| Sample Name | d (0.1) | d (0.5) | d (0.9) |
|---|---|---|---|
| Suspension 3, Measurement 1 | 28.54 | 133.06 | 256.35 |
| Suspension 3, Measurement 2 | 26.85 | 128.64 | 249.66 |
| Suspension 3, Measurement 3 | 26.09 | 126.42 | 244.15 |
| Average | 27.65 | 127.79 | 248.15 |

Example 14

Preparation of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide Form D Amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (30 g) was suspended in 200 mL of N,N-dimethylformamide, pre-heated to +20/25° C. After 5 minutes stirring a solution is obtained and after few minutes of stirring crystallization takes place. The suspension is stirred for about 2 hours. Then the suspension is cooled down to 0/+5° C. and stirred for about 2 hours.

Figure 25:
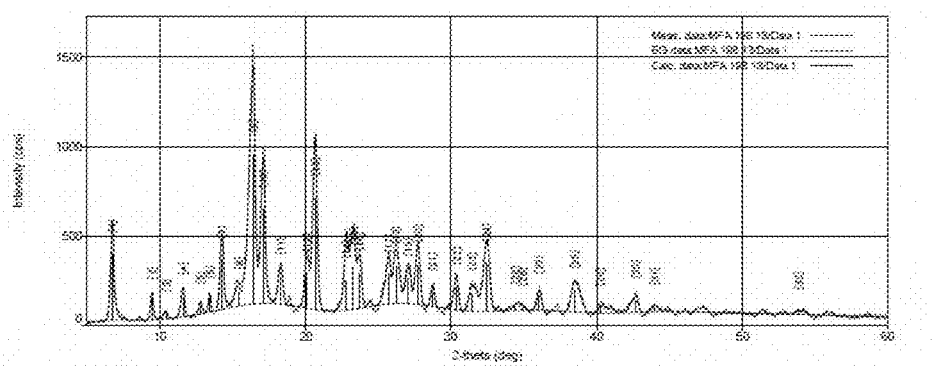
FIG. 25 is a X-ray powder diffraction pattern of Form D of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

The obtained solid is filtered and washed with 50 mL of N,N-dimethylformamide pre-cooled to 0/+5° C. The wet product is then suspended in 300 mL of dichloromethane and the temperature is adjusted to +30/32° C. The suspension is stirred for 45 minutes then the solid is filtered and washed with 100 mL of dichloromethane pre-heated to +30/32° C. The product is dried under vacuum at +40° C. until constant weight is achieved. The obtained product (19.3 g) was crystalline form D which was characterized by an XRPD pattern as shown in FIG. 25 and summarized in the following Table 11.

Figure 26:
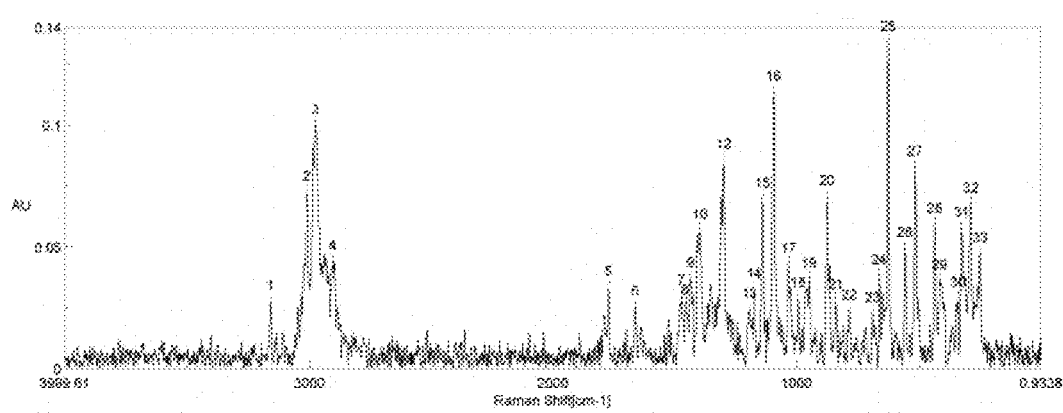
FIG. 26 is a Raman spectrum of Form D of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

The Raman spectrum of Form D is shown in FIG. 26 with the related peak band list in the following Table 12 (using Raman Jasco RFT-600 instrument, light source Nd-YAG, 1064 nm: exciting wavelength).

| Peak | Wave number | Y value |
|---|---|---|
| 1 | 3157.83 | 0.0281958 |
| 2 | 3009.34 | 0.072899 |
| 3 | 2974.63 | 0.100304 |
| 4 | 2904.24 | 0.0444922 |
| 5 | 1772.23 | 0.0339617 |
| 6 | 1663.27 | 0.0258104 |
| 7 | 1474.28 | 0.0302334 |
| 8 | 1458.85 | 0.0264177 |
| 9 | 1437.64 | 0.0373852 |
| 10 | 1400.04 | 0.0571817 |
| 11 | 1352.79 | 0.0302512 |
| 12 | 1302.65 | 0.0862235 |
| 13 | 1195.62 | 0.0247634 |
| 14 | 1175.37 | 0.0330307 |
| 15 | 1138.73 | 0.0701386 |
| 16 | 1092.45 | 0.11397 |
| 17 | 1031.7 | 0.0433419 |
| 18 | 993.13 | 0.0292598 |
| 19 | 947.811 | 0.0372661 |
| 20 | 874.529 | 0.0711543 |
| 21 | 838.853 | 0.028534 |
| 22 | 783.892 | 0.0241906 |
| 23 | 688.432 | 0.0231856 |
| 24 | 661.434 | 0.0387182 |
| 25 | 624.793 | 0.134281 |
| 26 | 556.332 | 0.0499649 |
| 27 | 514.87 | 0.0831978 |
| 28 | 433.875 | 0.0597285 |
| 29 | 414.59 | 0.0366139 |
| 30 | 340.344 | 0.0295258 |
| 31 | 324.916 | 0.058052 |

| No. | Angle [°2θ] | d-spacing [Å] | Height (cps) | FWHM (deg) | Int. | deg | Int. |
|---|---|---|---|---|---|---|---|
| 1 | 6.7824 | 13.02204 | 369.45 | 0.2491 | 119.22 | 0.3227 | 333.64 |
| 2 | 9.5032 | 9.29904 | 105.18 | 0.2064 | 26.05 | 0.2477 | 403.40 |
| 3 | 10.4510 | 8.45774 | 31.17 | 0.2565 | 10.15 | 0.3256 | 324.89 |
| 4 | 11.6074 | 7.61762 | 109.02 | 0.2733 | 31.72 | 0.2910 | 305.11 |
| 5 | 12.7850 | 6.91847 | 41.58 | 0.2692 | 11.91 | 0.2865 | 310.18 |
| 6 | 13.4325 | 6.58642 | 64.83 | 0.2025 | 13.98 | 0.2156 | 412.47 |
| 7 | 14.2560 | 6.20776 | 275.43 | 0.2923 | 86.51 | 0.3141 | 286.05 |
| 8 | 15.4567 | 5.72810 | 77.92 | 1.8085 | 152.28 | 1.9543 | 46.30 |
| 9 | 16.3961 | 5.40199 | 835.69 | 0.4340 | 388.58 | 0.4650 | 193.15 |
| 10 | 17.1082 | 5.17871 | 522.62 | 0.3370 | 188.77 | 0.3612 | 249.00 |
| 11 | 18.2742 | 4.85081 | 148.14 | 0.3388 | 53.91 | 0.3639 | 248.02 |
| 12 | 20.0651 | 4.42173 | 194.88 | 0.5228 | 109.82 | 0.5635 | 161.19 |
| 13 | 20.6373 | 4.30040 | 624.11 | 0.3160 | 211.90 | 0.3395 | 266.91 |
| 14 | 22.7520 | 3.90524 | 167.10 | 0.2473 | 44.02 | 0.2635 | 342.21 |
| 15 | 23.2376 | 3.82472 | 236.56 | 0.6238 | 157.13 | 0.6642 | 135.79 |
| 16 | 23.6811 | 3.75409 | 198.42 | 0.5077 | 107.27 | 0.5406 | 167.00 |
| 17 | 25.6817 | 3.46600 | 163.48 | 0.4133 | 71.93 | 0.4400 | 205.89 |
| 18 | 26.1802 | 3.40112 | 205.89 | 0.5004 | 109.66 | 0.5326 | 170.25 |
| 19 | 26.9957 | 3.30020 | 138.32 | 0.4481 | 65.98 | 0.4770 | 190.41 |
| 20 | 27.7606 | 3.21098 | 221.24 | 0.3671 | 86.44 | 0.3907 | 232.85 |
| 21 | 28.7686 | 3.10073 | 75.61 | 0.2697 | 21.70 | 0.2870 | 317.65 |
| 22 | 30.4020 | 2.93775 | 125.52 | 0.3451 | 46.72 | 0.3722 | 249.17 |
| 23 | 31.4633 | 2.84104 | 102.42 | 0.6496 | 72.49 | 0.7078 | 132.70 |
| 24 | 32.4753 | 2.75478 | 268.97 | 0.4635 | 134.78 | 0.5011 | 186.43 |
| 25 | 34.4252 | 2.60307 | 21.60 | 0.6492 | 14.92 | 0.6911 | 133.80 |
| 26 | 34.9492 | 2.56524 | 12.83 | 0.4399 | 6.01 | 0.4682 | 197.76 |
| 27 | 36.0489 | 2.48946 | 80.97 | 0.3230 | 27.84 | 0.3438 | 270.15 |
| 28 | 38.4794 | 2.33762 | 119.18 | 0.6568 | 83.33 | 0.6992 | 133.80 |
| 29 | 40.2292 | 2.23989 | 27.09 | 0.9554 | 27.55 | 1.0170 | 92.49 |
| 30 | 42.6703 | 2.11723 | 63.61 | 0.5331 | 36.10 | 0.5675 | 167.09 |
| 31 | 43.9731 | 2.05748 | 22.45 | 0.4622 | 11.29 | 0.5030 | 193.59 |
| 32 | 53.8897 | 1.69994 | 16.28 | 0.5850 | 11.95 | 0.7339 | 159.10 |

-continued

| Peak | Wave number | Y value |
|---|---|---|
| 32 | 287.311 | 0.0680197 |
| 33 | 249.706 | 0.0476452 |

Example 15

Preparation of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide Form E Amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (5 g) was suspended in 30 mL of N,N-dimethylformamide, pre-heated to +20/25° C. After 5 minutes of stirring, a solution is obtained and after few minutes a crystallization takes place. The suspension is stirred for about 2 hours.

The obtained solid is filtered and washed with 12.5 mL of N,N-dimethylformamide. The wet product is then suspended in 100 mL of ethyl acetate and the temperature is adjusted to +40/45° C. The suspension is stirred for 60 minutes then the solid is filtered and washed with 50 mL of ethyl acetate pre-heated to +40/45° C.

Finally the product is dried under vacuum at +40° C. till constant weight is achieved.

Figure 27:
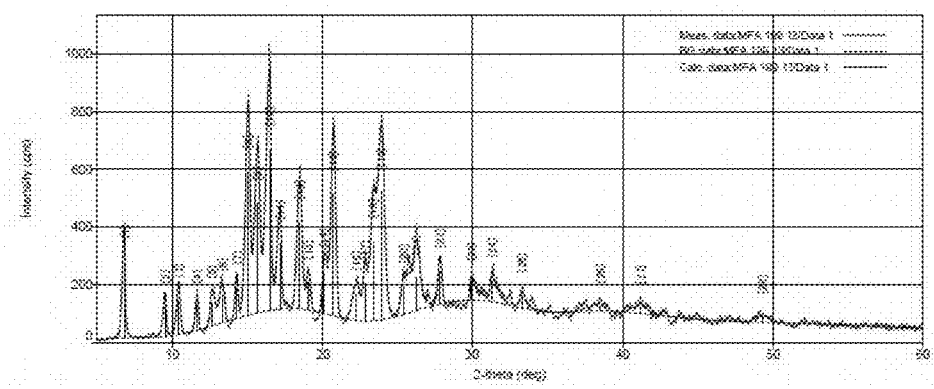
FIG. 27 is a X-ray powder diffraction pattern of Form E of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

The obtained product (2.4 g) was crystalline form E which was characterized by an XRPD pattern as shown in FIG. 27 and summarized in the following Table 13.

Figure 28:
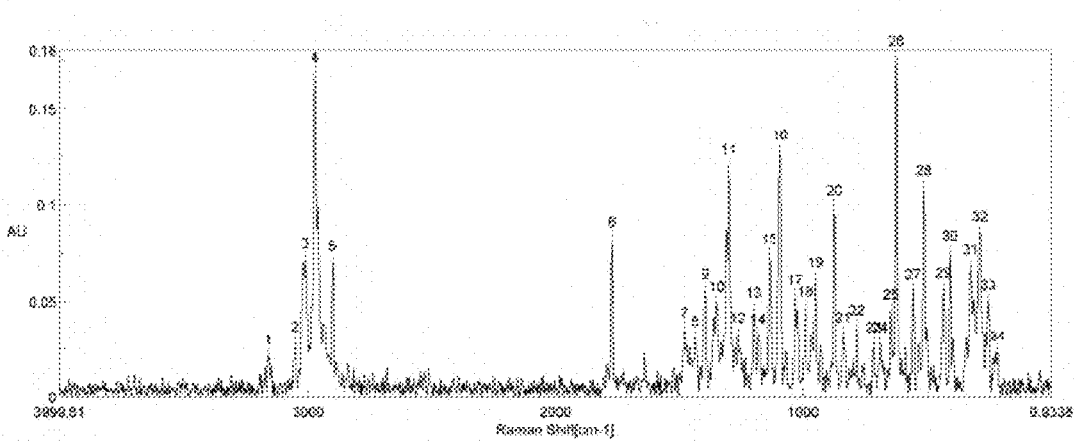
FIG. 28 is a Raman spectrum of Form E of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

The Raman spectrum of Form E is shown in FIG. 28 with the related peak band list in the following Table 14 (using Raman Jasco RFT-600 instrument, light source Nd-YAG, 1064 nm: exciting wavelength).

| Peak | Wave number | Y value |
|---|---|---|
| 1 | 3158.8 | 0.0221892 |
| 2 | 3051.77 | 0.0289691 |
| 3 | 3011.27 | 0.0722239 |
| 4 | 2973.67 | 0.168653 |
| 5 | 2900.38 | 0.0707581 |
| 6 | 1772.23 | 0.0829712 |
| 7 | 1482 | 0.036189 |
| 8 | 1438.61 | 0.0318463 |
| 9 | 1397.14 | 0.0563706 |
| 10 | 1352.79 | 0.0498639 |
| 11 | 1302.65 | 0.120509 |
| 12 | 1266.01 | 0.0335002 |
| 13 | 1202.37 | 0.0466914 |
| 14 | 1185.01 | 0.0332323 |
| 15 | 1139.69 | 0.0742465 |
| 16 | 1092.45 | 0.128341 |
| 17 | 1031.7 | 0.0532132 |
| 18 | 989.273 | 0.0474664 |
| 19 | 949.74 | 0.0622083 |
| 20 | 873.565 | 0.0993489 |
| 21 | 836.924 | 0.0338838 |
| 22 | 782.927 | 0.0376849 |
| 23 | 715.431 | 0.0287148 |
| 24 | 589.397 | 0.028656 |
| 25 | 646.006 | 0.0458421 |
| 26 | 624.793 | 0.177092 |
| 27 | 556.332 | 0.0561384 |
| 28 | 613.906 | 0.109643 |
| 29 | 433.875 | 0.0568177 |
| 30 | 407.84 | 0.0759362 |
| 31 | 325.881 | 0.68886 |
| 32 | 288.276 | 0.0859623 |
| 33 | 254.527 | 0.050626 |
| 34 | 216.922 | 0.0240766 |

| No. | Angle [°2θ] | d-spacing [Å] | Height (cps) | FWHM (deg) | Int. | deg) | Int. |
|---|---|---|---|---|---|---|---|
| 1 | 6.8269 | 12.93732 | 260.98 | 0.2205 | 68.42 | 0.2622 | 376.99 |
| 2 | 9.5377 | 9.26545 | 102.12 | 0.2256 | 29.95 | 0.2933 | 369.14 |
| 3 | 10.4196 | 8.48314 | 117.20 | 0.2867 | 38.29 | 0.3267 | 290.56 |
| 4 | 11.6525 | 7.58825 | 82.26 | 0.2299 | 20.13 | 0.2447 | 362.76 |
| 5 | 12.6274 | 7.00451 | 83.34 | 0.3681 | 32.66 | 0.3919 | 226.76 |
| 6 | 13.3413 | 6.63125 | 95.57 | 0.3884 | 39.52 | 0.4135 | 215.07 |
| 7 | 14.2802 | 6.19726 | 104.47 | 0.2212 | 26.92 | 0.2577 | 378.06 |
| 8 | 15.0475 | 5.88296 | 494.41 | 0.3508 | 199.68 | 0.4039 | 238.55 |
| 9 | 15.6848 | 5.64531 | 378.40 | 0.3968 | 173.35 | 0.4581 | 211.11 |
| 10 | 16.4735 | 5.37678 | 557.04 | 0.3770 | 234.97 | 0.4218 | 222.38 |
| 11 | 17.1773 | 5.15801 | 229.03 | 0.3175 | 81.31 | 0.3550 | 264.28 |
| 12 | 18.4488 | 4.80530 | 297.04 | 0.3867 | 122.28 | 0.4117 | 217.36 |
| 13 | 19.0164 | 4.66312 | 93.86 | 0.2902 | 28.99 | 0.3089 | 289.90 |
| 14 | 20.0808 | 4.41830 | 143.91 | 0.4955 | 75.93 | 0.5276 | 170.05 |
| 15 | 20.6999 | 4.28752 | 421.62 | 0.3301 | 148.17 | 0.3514 | 255.52 |
| 16 | 22.2167 | 3.99811 | 90.66 | 0.6225 | 62.16 | 0.6857 | 135.85 |
| 17 | 22.7863 | 3.89944 | 130.42 | 0.4242 | 61.57 | 0.4721 | 199.52 |
| 18 | 23.3436 | 3.80760 | 273.25 | 0.4007 | 120.48 | 0.4409 | 211.43 |
| 19 | 23.8843 | 3.72261 | 447.75 | 0.4942 | 242.53 | 0.5417 | 171.61 |
| 20 | 25.3818 | 3.50627 | 95.40 | 1.0693 | 109.22 | 1.1449 | 79.54 |
| 21 | 26.2231 | 3.39566 | 113.17 | 0.5204 | 63.45 | 0.5606 | 163.70 |
| 22 | 27.8574 | 3.20005 | 112.17 | 0.2916 | 35.41 | 0.3157 | 293.14 |
| 23 | 29.9383 | 2.98219 | 52.64 | 0.4091 | 38.32 | 0.7279 | 209.96 |
| 24 | 31.3100 | 2.85459 | 70.72 | 0.3247 | 40.45 | 0.5720 | 265.41 |
| 25 | 33.3041 | 2.68809 | 41.89 | 0.3114 | 17.99 | 0.4295 | 278.15 |
| 26 | 38.5117 | 2.33574 | 15.66 | 1.2693 | 21.16 | 1.3512 | 69.24 |
| 27 | 41.1953 | 2.18957 | 21.01 | 1.1036 | 24.69 | 1.1748 | 80.32 |
| 28 | 49.2559 | 1.84846 | 16.52 | 0.9722 | 17.90 | 1.0835 | 93.88 |

Example 16

Preparation of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide Form F Amorphous (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (130 g) was suspended in 800 mL of N,N-dimethylformamide, pre-heated to +20/25° C. 100 mL of N,N-dimethylformamide was added to wash the walls of the flask. After 5 minutes stirring a solution is obtained and after few minutes of stirring crystallization takes place. The suspension is stirred for about 3 hours. Then the suspension is cooled down to 0/+5° C. and stirred for about 3 hours.

The obtained solid is filtered and washed with 300 mL of N,N-dimethylformamide pre-cooled to 0/+5° C. The wet product is then suspended in 700 mL of ethyl acetate and the temperature is adjusted to +40/45° C. The suspension is stirred for 30 minutes then the solid is filtered and washed with 150 mL of ethyl acetate pre-heated to +40/45° C. The procedure with the suspension in Ethyl acetate is repeated twice. Finally the product is dried under vacuum at +40° C. till constant weight is achieved.

Figure 29:
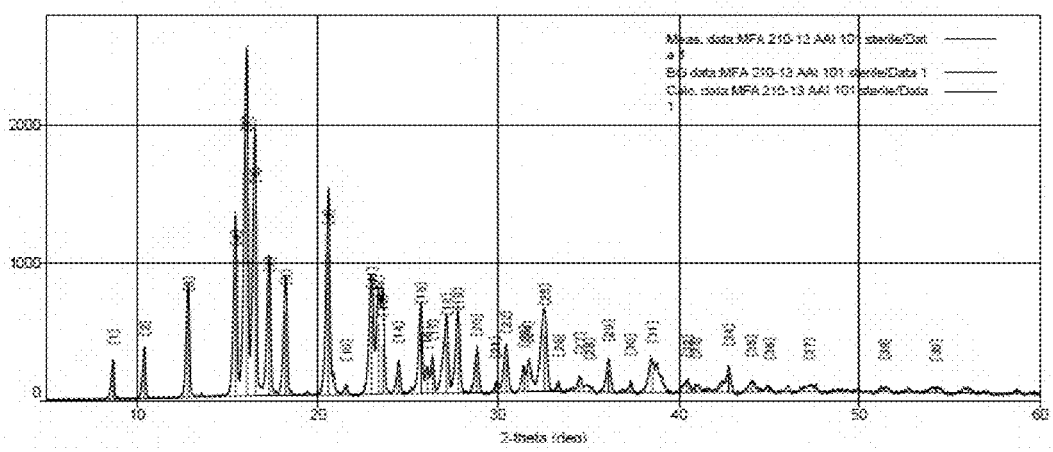
FIG. 29 is a X-ray powder diffraction pattern of Form F of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

The obtained product (65-66 g, molar yield about 76%, with an assay of 98-99% was crystalline form F, which was characterized by an XRPD pattern as shown in FIG. 29 and summarized in the following Table 15.

Figure 30:
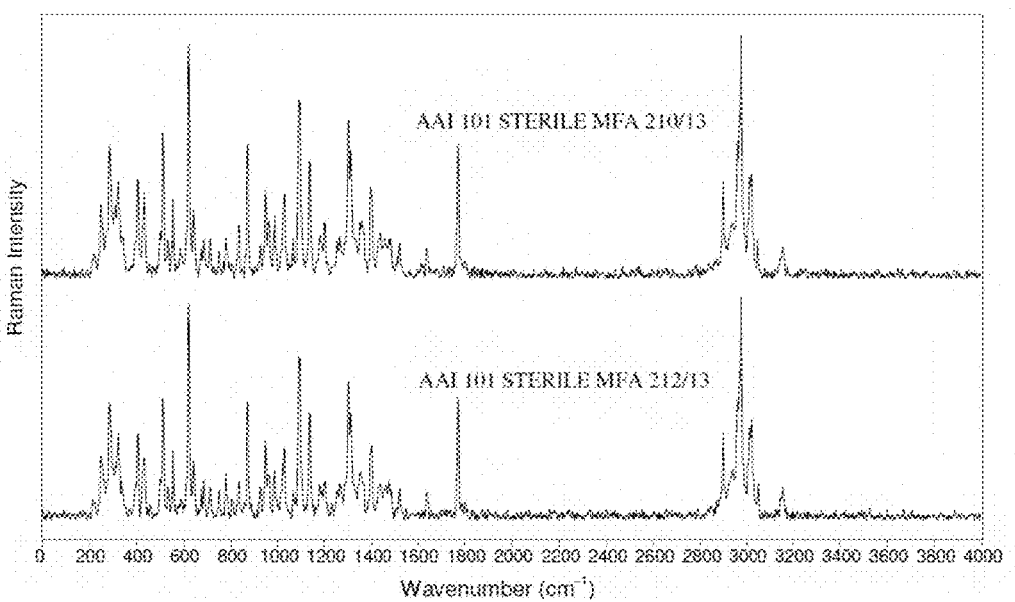
FIGS. 30 and 31 are Raman spectra of three bathes of Form F of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.
Figure 31:
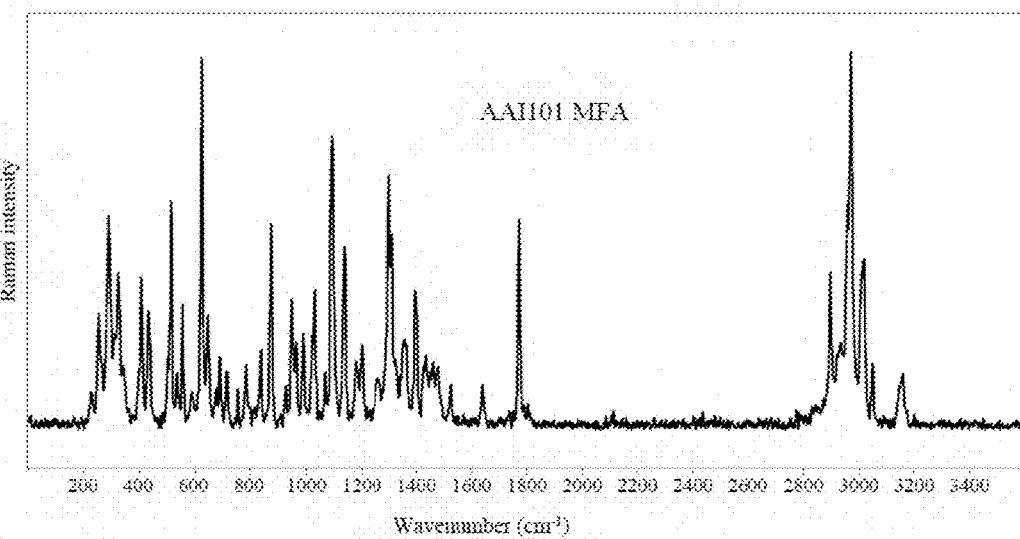
Figure 32:
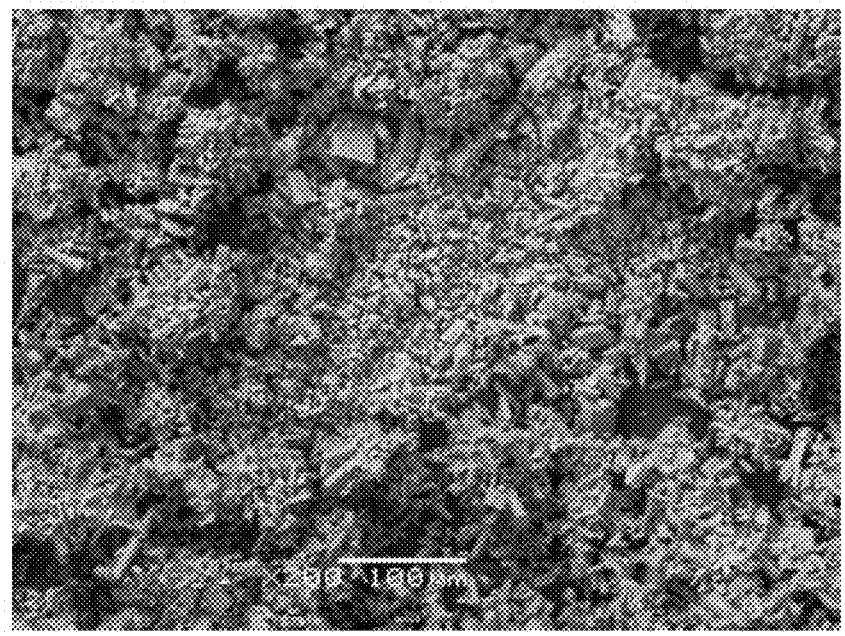
FIGS. 32-39 are scanning electron microscopy images of samples of a first batch of Form F of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.
Figure 33:
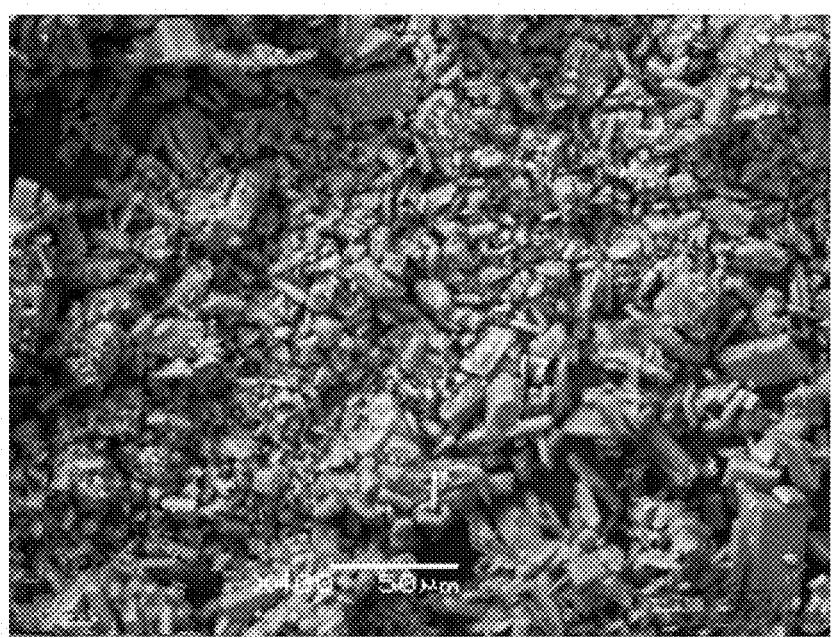
Figure 34:
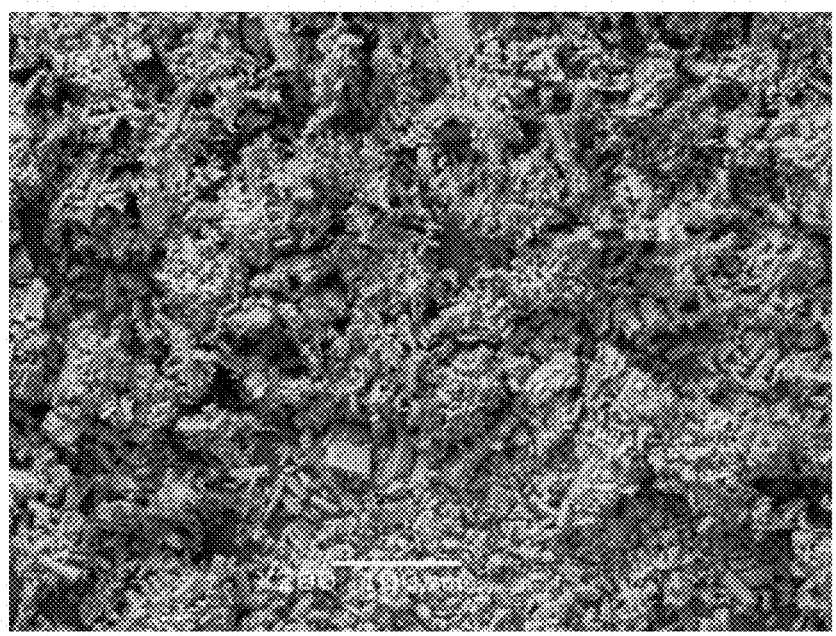
Figure 35:
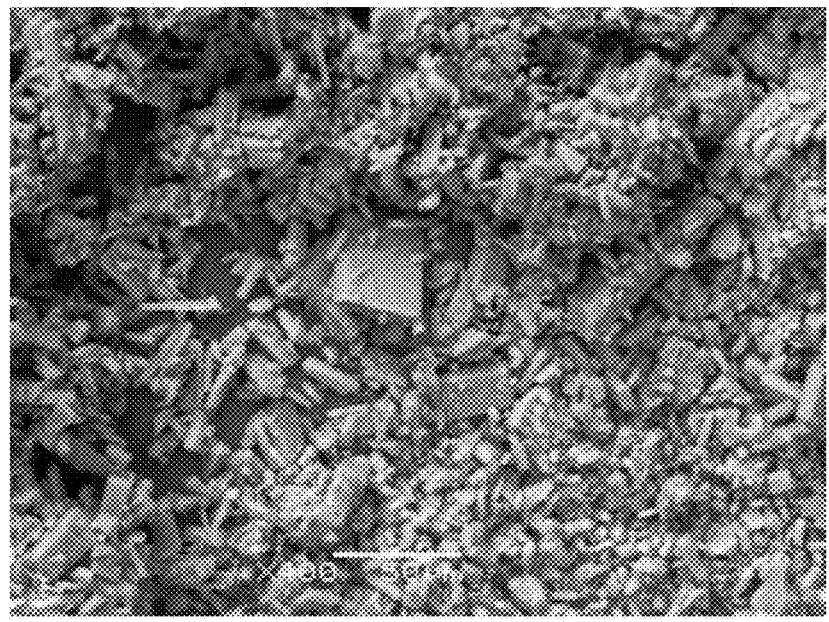
Figure 36:
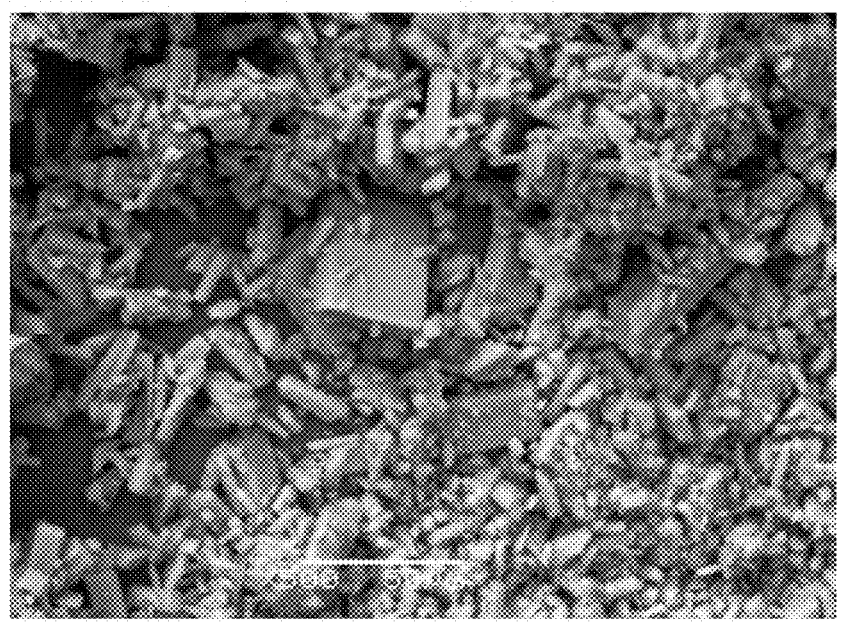
Figure 37:
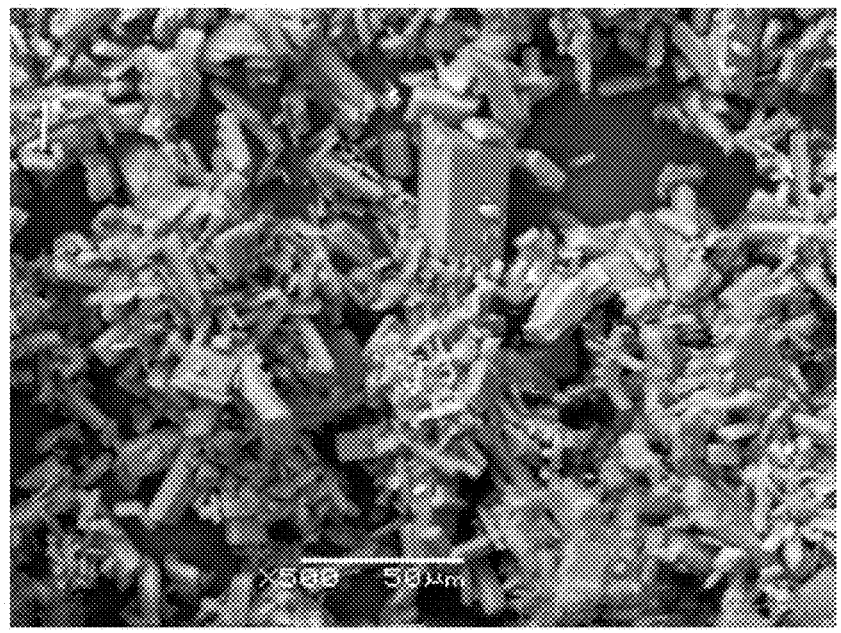
Figure 38:
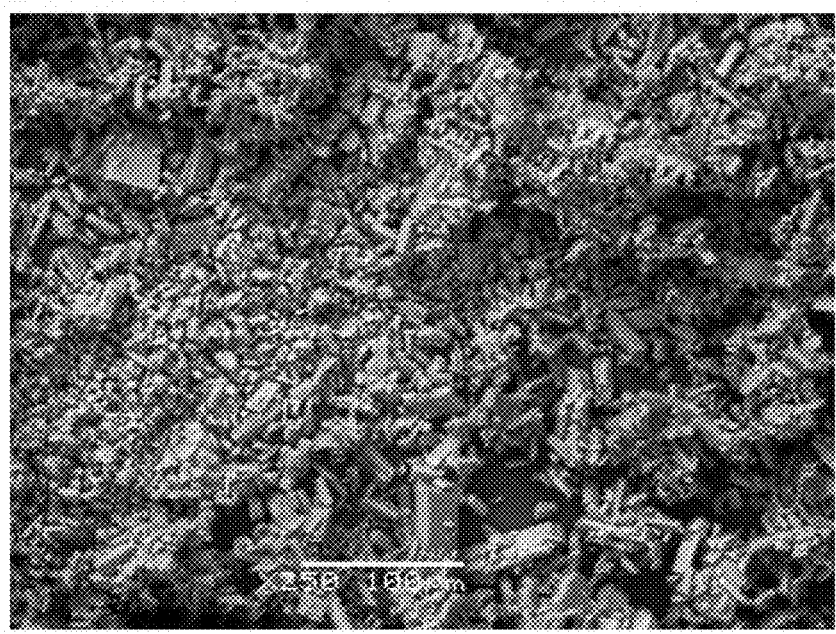
Figure 39:
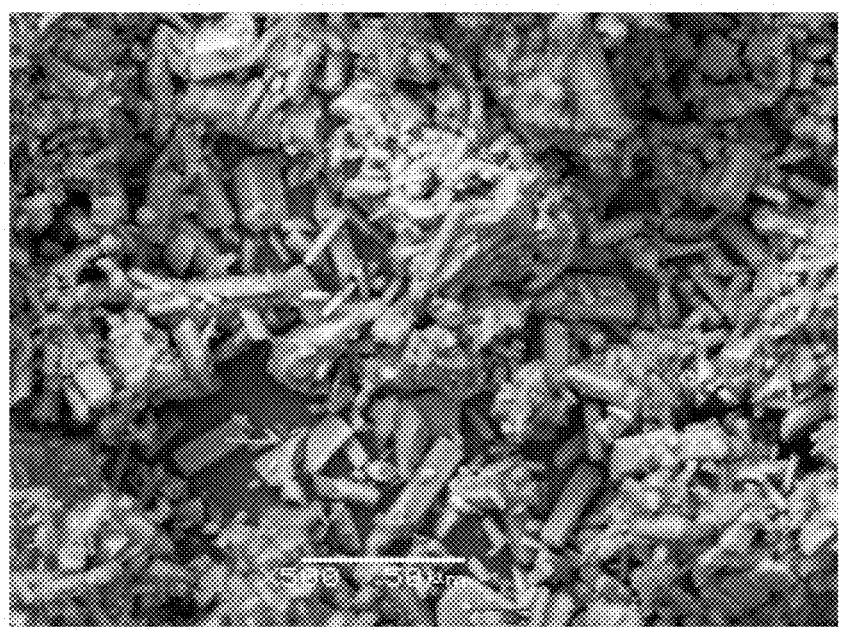
Figure 40:
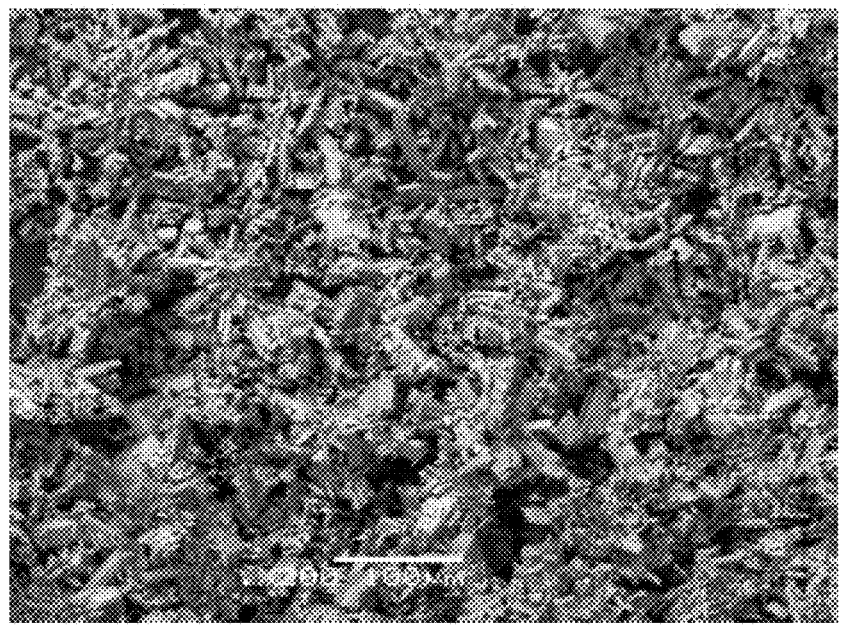
FIGS. 40-46 are scanning electron microscopy images of samples of a second batch of Form F of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.
Figure 41:
Figure 42:
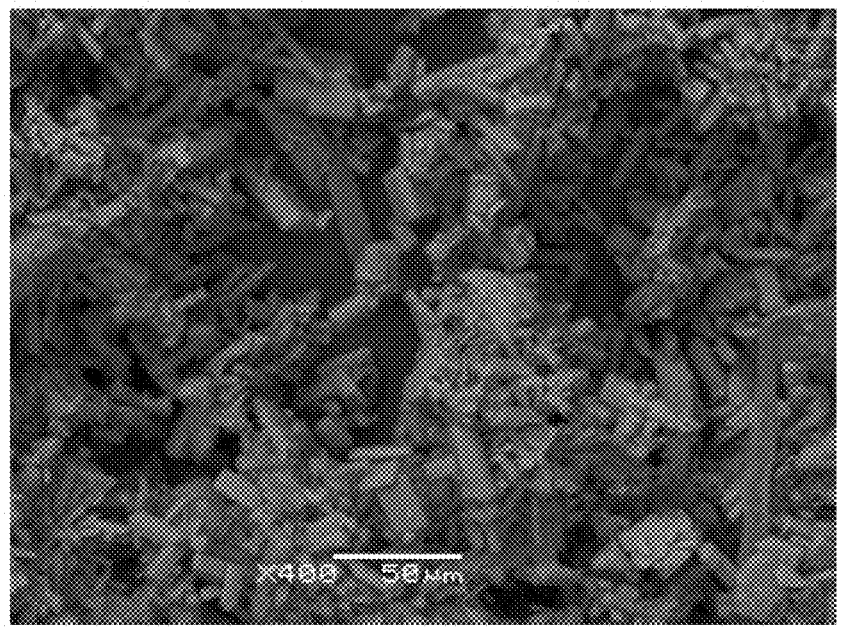
Figure 43:
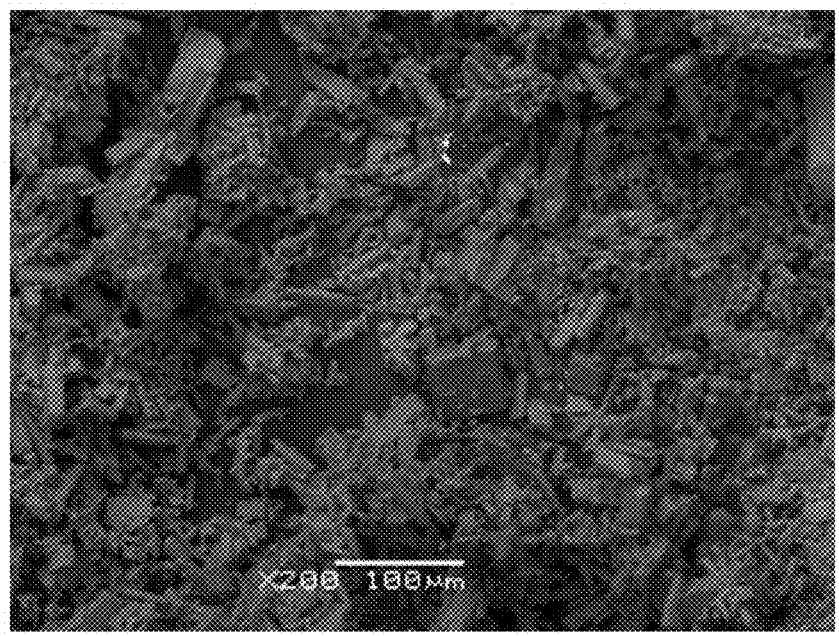
Figure 44:
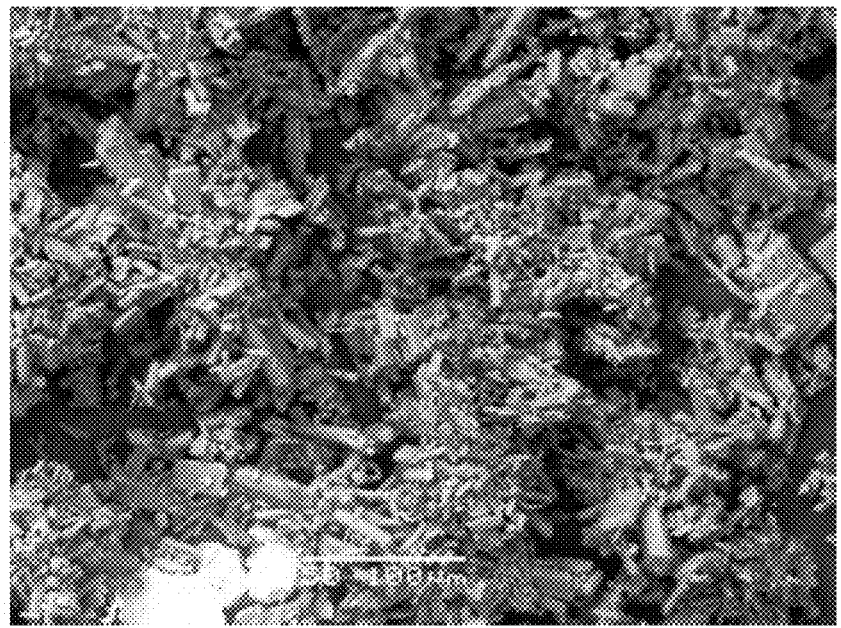
Figure 45:
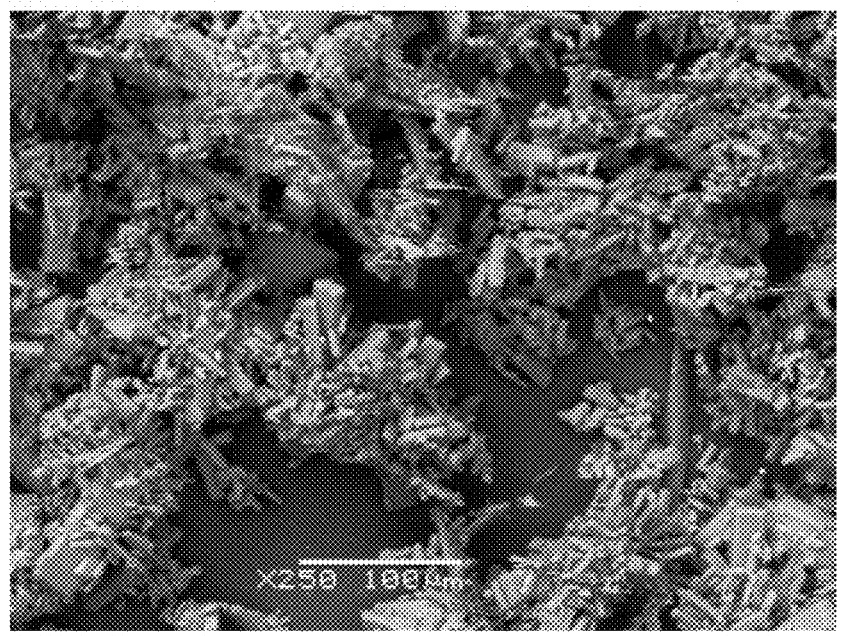
Figure 46:
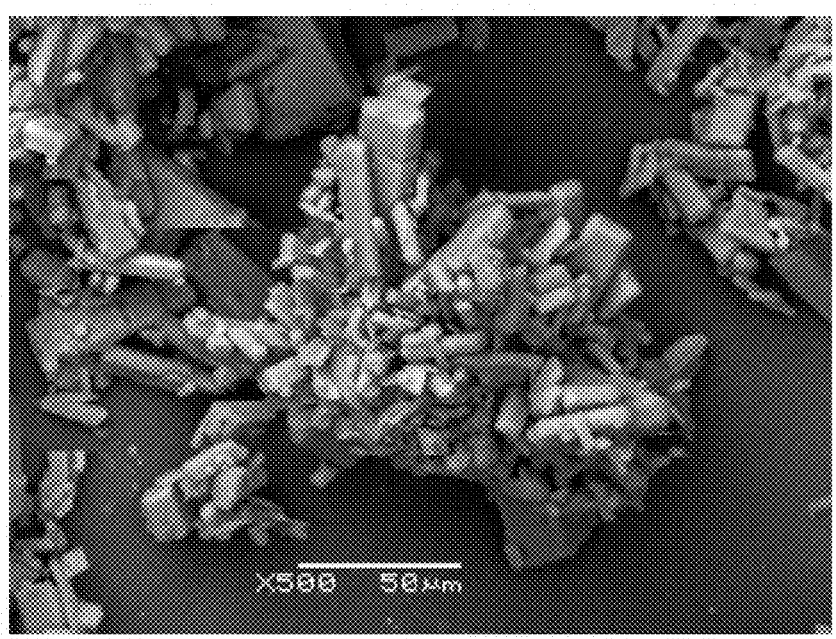
Figure 47:
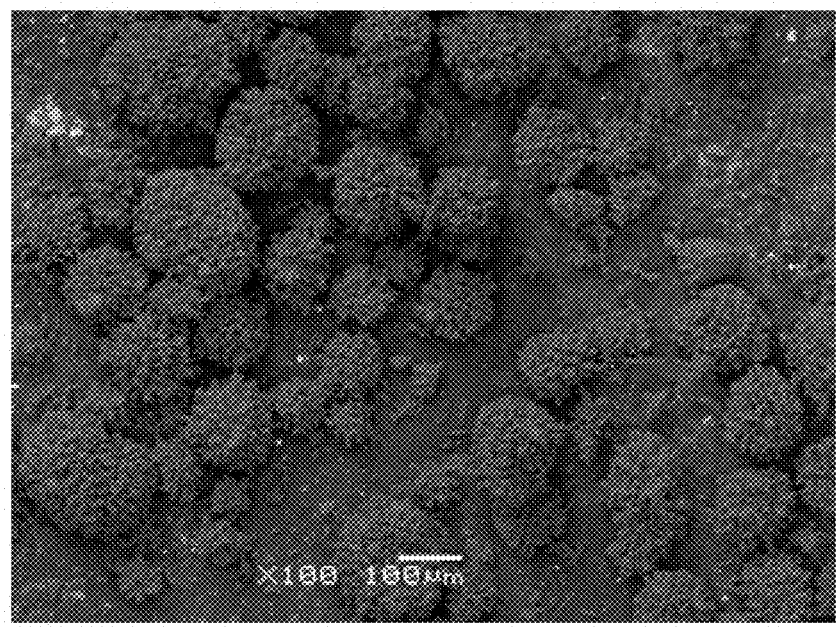
FIGS. 47-50 are scanning electron microscopy images of samples of a third batch of Form F of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.
Figure 48:
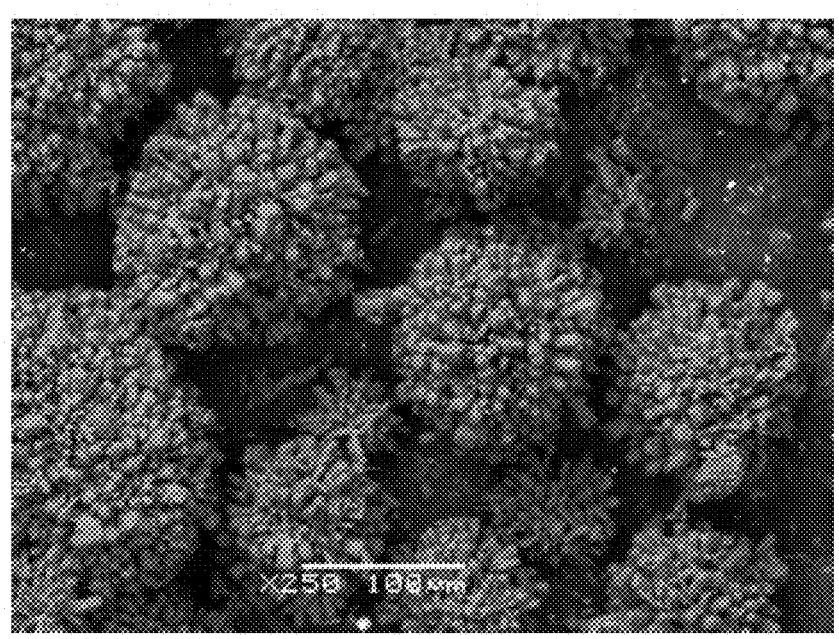
Figure 49:
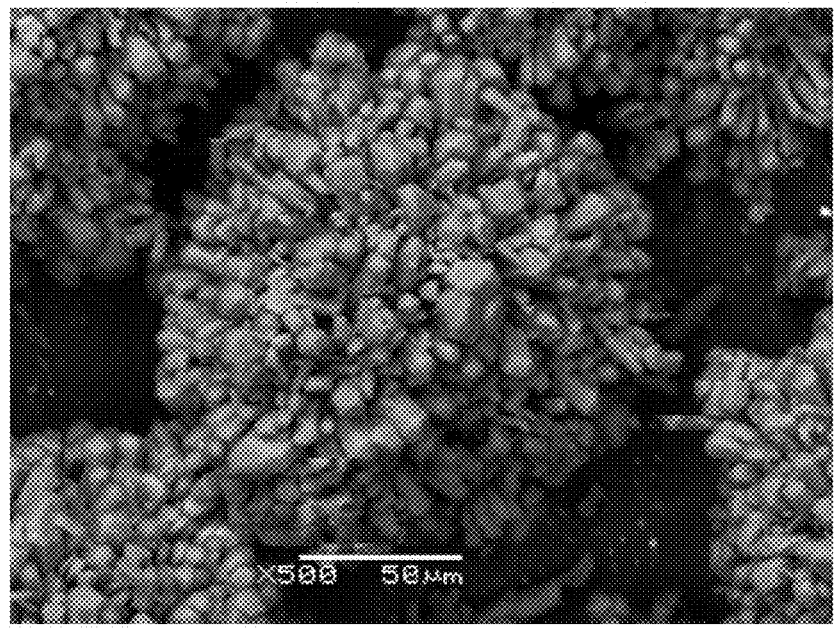
Figure 50:
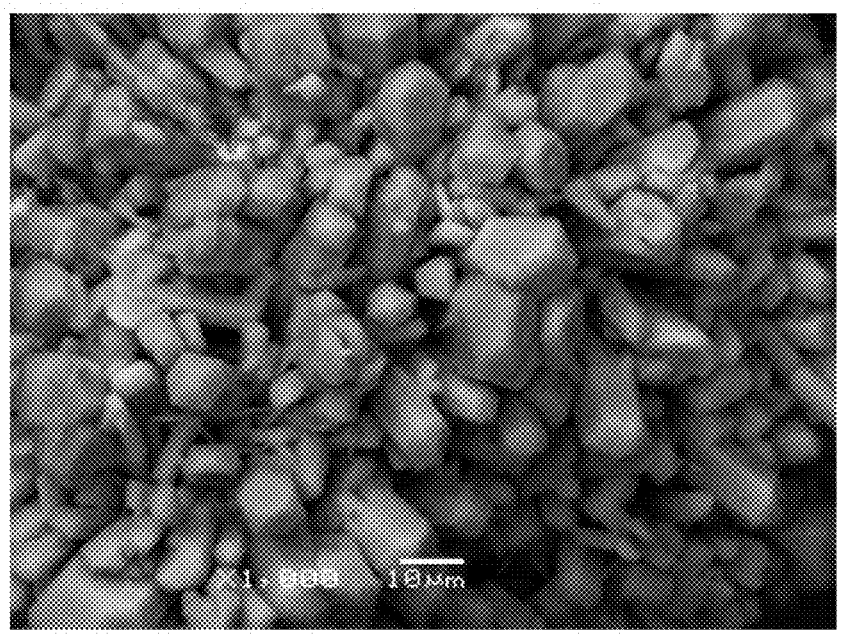

Raman spectra for three bathes of Form F are shown in FIGS. 30 and 31.

Both XRPD and Raman spectra acquired for different batches of Form F product are overlapping.

Scanning electron microscopy images of samples of the three batches of Form F are shown in FIGS. 32-50. The SEM images of the samples were obtained using a JEOL JSM 5500 LV scanning electron microscope, operating at 30 kV in low vacuum (30 Pa) with the backscattered electron technique.

Form F characterization by FT-IR, DSC, TGA, EGA

Figure 51:
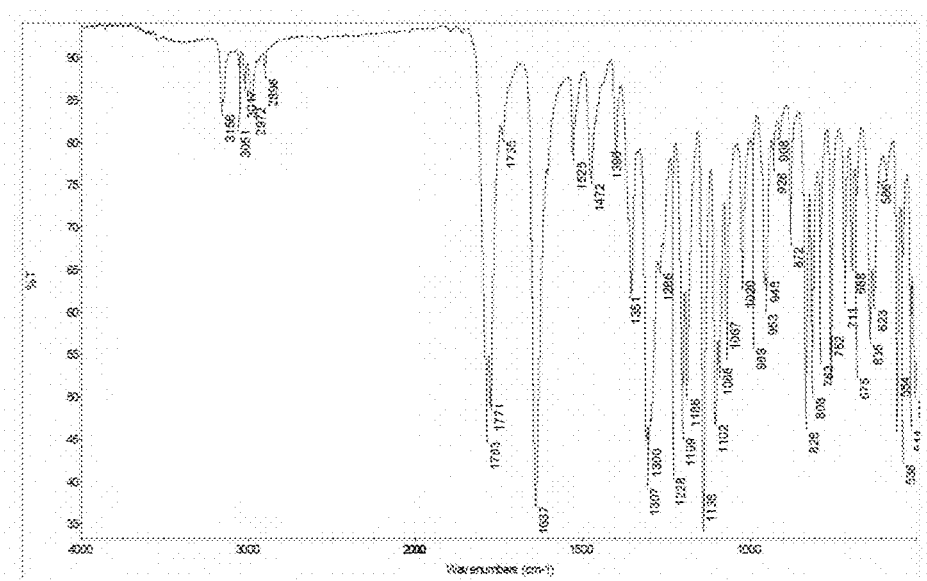
FIG. 51 is a FT-RT spectrum of Form F of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

FIG. 51 shows the FT-IR spectrum of Form F with the related peak bands list in Table 16.

Peak List:

| Position | Intensity |
| --- | --- |
| 502 | 50.668 |
| 514 | 59.193 |
| 538 | 66.311 |
| 554 | 48.279 |
| 586 | 76.021 |
| 623 | 60.523 |
| 635 | 58.506 |
| 675 | 73.819 |
| 688 | 65.213 |
| 711 | 63.330 |
| 752 | 53.517 |
| 783 | 68.207 |
| 808 | 55.605 |
| 826 | 52.413 |
| 872 | 72.360 |

| No. | Angle [°2θ] | d-spacing [Å] | Height (cps) | FWHM (deg) | Int. | deg | Int. |
| --- | --- | --- | --- | --- | --- | --- | --- |
| 1 | 8.5718 | 10.30725 | 116.72 | 0.1981 | 26.19 | 0.2244 | 419.96 |
| 2 | 10.3165 | 8.56773 | 182.16 | 0.2142 | 42.67 | 0.2343 | 388.97 |
| 3 | 12.7398 | 6.94292 | 420.49 | 0.2216 | 103.83 | 0.2469 | 376.75 |
| 4 | 15.3615 | 5.76339 | 870.60 | 0.2471 | 241.26 | 0.2771 | 338.84 |
| 5 | 15.9547 | 5.55042 | 1374.98 | 0.2605 | 400.47 | 0.2913 | 321.60 |
| 6 | 16.4290 | 5.39123 | 1343.96 | 0.2344 | 352.88 | 0.2626 | 357.69 |
| 7 | 17.1990 | 5.15158 | 477.25 | 0.2281 | 118.86 | 0.2490 | 367.89 |
| 8 | 18.1207 | 4.89155 | 531.20 | 0.2398 | 146.12 | 0.2751 | 350.36 |
| 9 | 20.4870 | 4.33160 | 915.19 | 0.2443 | 275.10 | 0.3006 | 345.16 |
| 10 | 21.4040 | 4.14805 | 37.20 | 0.1769 | 7.01 | 0.1884 | 477.23 |
| 11 | 22.8548 | 3.88791 | 528.69 | 0.2904 | 164.14 | 0.3105 | 291.53 |
| 12 | 23.2204 | 3.82751 | 502.41 | 0.3500 | 188.64 | 0.3755 | 242.00 |
| 13 | 23.4688 | 3.78756 | 292.42 | 0.1501 | 47.04 | 0.1609 | 564.73 |
| 14 | 24.4199 | 3.64215 | 132.35 | 0.2404 | 34.95 | 0.2641 | 353.09 |
| 15 | 25.6394 | 3.47163 | 359.02 | 0.2563 | 104.03 | 0.2897 | 331.96 |
| 16 | 25.9983 | 3.42450 | 94.56 | 0.2531 | 27.13 | 0.2869 | 336.47 |
| 17 | 26.2914 | 3.38699 | 134.69 | 0.2951 | 45.04 | 0.3344 | 288.79 |
| 18 | 27.0457 | 3.29421 | 387.38 | 0.3463 | 151.47 | 0.3910 | 246.47 |
| 19 | 27.6934 | 3.21862 | 412.53 | 0.2941 | 136.95 | 0.3320 | 290.62 |
| 20 | 28.7394 | 3.10381 | 190.86 | 0.2739 | 56.91 | 0.2982 | 312.74 |
| 21 | 29.7603 | 2.99962 | 32.77 | 0.2736 | 9.54 | 0.2913 | 313.76 |
| 22 | 30.3078 | 2.94667 | 222.03 | 0.2854 | 67.46 | 0.3038 | 301.19 |
| 23 | 31.4660 | 2.84080 | 125.87 | 0.5371 | 71.97 | 0.5717 | 160.49 |
| 24 | 32.3054 | 2.76888 | 98.55 | 0.2002 | 21.00 | 0.2131 | 431.51 |
| 25 | 32.4785 | 2.75451 | 363.46 | 0.4069 | 157.43 | 0.4331 | 212.38 |
| 26 | 33.1981 | 2.69643 | 37.54 | 0.2403 | 9.60 | 0.2558 | 360.31 |
| 27 | 33.7446 | 2.65401 | 15.05 | 0.5057 | 8.10 | 0.5383 | 171.46 |
| 28 | 34.3283 | 2.61020 | 55.64 | 0.1955 | 11.58 | 0.2081 | 444.20 |
| 29 | 35.0200 | 2.56021 | 21.77 | 0.6046 | 14.01 | 0.6435 | 143.92 |
| 30 | 35.9880 | 2.49354 | 133.13 | 0.2751 | 38.98 | 0.2928 | 317.16 |
| 31 | 38.4256 | 2.34077 | 142.45 | 0.6826 | 103.50 | 0.7266 | 128.73 |
| 32 | 40.2911 | 2.23659 | 56.34 | 0.4183 | 25.09 | 0.4453 | 211.28 |
| 33 | 40.8969 | 2.20485 | 33.86 | 0.3473 | 12.52 | 0.3697 | 254.95 |
| 34 | 42.6047 | 2.12034 | 130.78 | 0.2718 | 59.44 | 0.4545 | 327.66 |
| 35 | 43.7327 | 2.06823 | 39.36 | 0.5339 | 22.37 | 0.5684 | 167.46 |
| 36 | 44.8088 | 2.02103 | 29.53 | 0.2009 | 6.31 | 0.2138 | 446.84 |
| 37 | 53.9562 | 1.69800 | 23.47 | 0.6255 | 15.68 | 0.6680 | 148.86 |

-continued

| Position | Intensity |
|----------|-----------|
| 908 | 81.158 |
| 928 | 78.947 |
| 948 | 62.908 |
| 953 | 63.041 |
| 989 | 78.973 |
| 1020 | 62.785 |
| 1067 | 55.907 |
| 1088 | 52.453 |
| 1102 | 46.426 |
| 1136 | 35.517 |
| 1186 | 50.232 |
| 1199 | 50.943 |
| 1228 | 75.847 |
| 1266 | 64.974 |
| 1300 | 44.572 |
| 1307 | 44.644 |
| 1351 | 62.003 |
| 1396 | 78.685 |
| 1472 | 75.504 |
| 1525 | 78.318 |
| 1637 | 36.877 |
| 1735 | 80.927 |
| 1771 | 48.478 |
| 1783 | 51.962 |
| 2898 | 88.274 |
| 2972 | 84.793 |
| 3017 | 86.781 |
| 3051 | 88.751 |
| 3156 | 84.061 |

Figure 52:
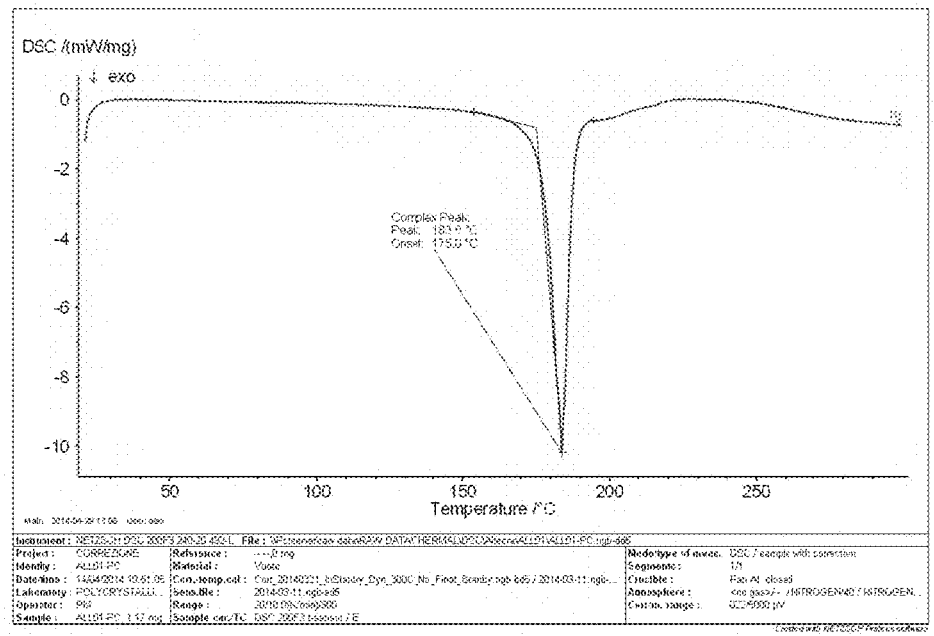
FIG. 52 is a differential scanning calorimetric thermogram of Form F of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

The DSC profile of form F is presented in FIG. 52. The DSC profile shows an exothermic peak at approximately 184° C. (Onset 175° C.) associated with the degradation of the sample.

Figure 53:
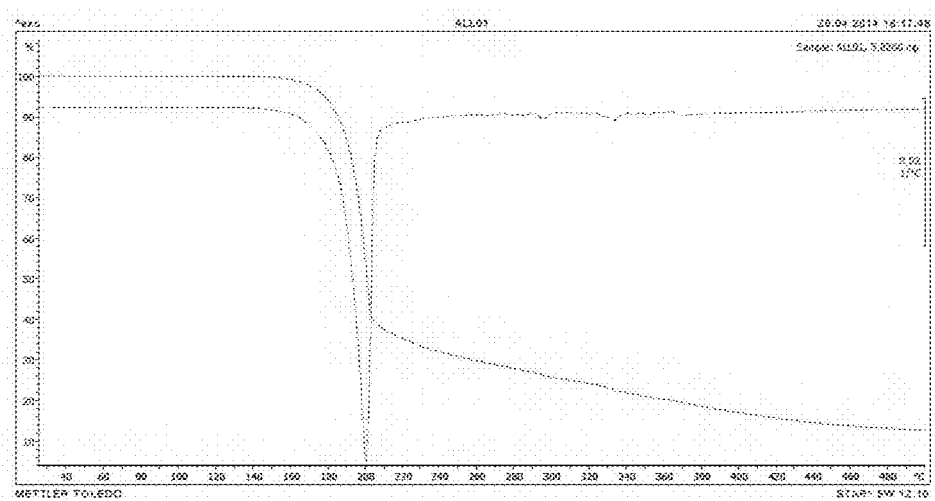
FIG. 53 is a thermogravimetric curve of Form F of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.
Figure 54:
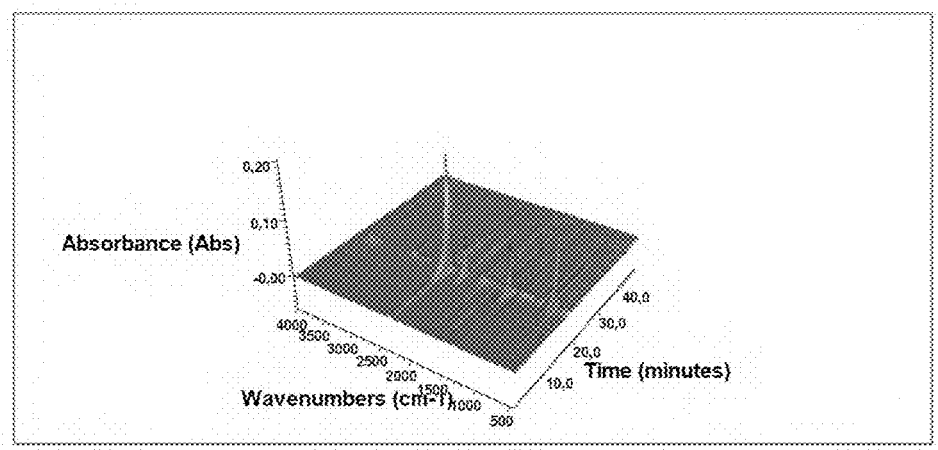
FIG. 54 is a gas evolution image of Evolved Gas Analysis (EGA) of Form F of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

The Thermo Gravimetric Analysis (TGA) profile of Form F presented on FIG. 53 shows a significant weight loss after approximately 160° C. associated with the degradation of the sample. That is further confirmed by an Evolved Gas Analysis (EGA) shown in FIG. 54. The EGA evidences that the event observed in TGA analysis is caused by the loss of degradation products (e.g. carbon dioxide, sulphur dioxide, etc).

Form F Characterization by Dynamic Vapor Sorption (DVS)

Figure 55:
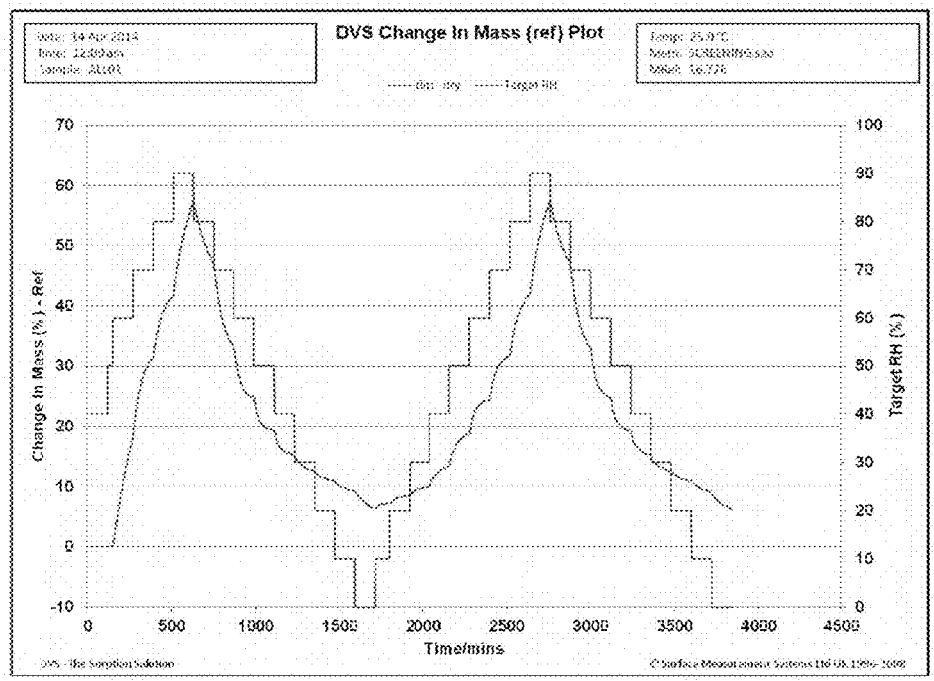
FIG. 55 is a plot of Dynamic Vapor Sorption (DVS) change in mass of Form F of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

Kinetic moisture sorption measurements were performed at 25° C. and at relative humidity (RH % target as follows:
From 40% RH to 90% RH
Form 90% RH to 0% RH
From 0% RH to 90% RH
From 90% RH to 0% RH The obtained results are presented in FIG. 55, wherein the red line traces the percentage changes in mass as function of the time, while the blue line traces the relative humidity changes as function of the time.

Figure 56:
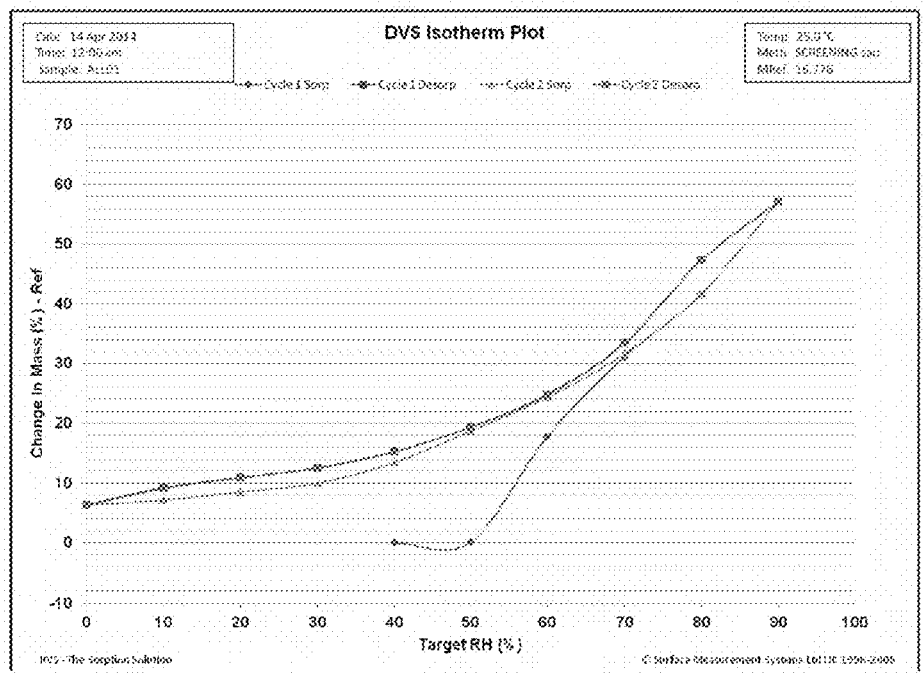
FIG. 56 shows Dynamic Vapor Sorption (DVS) isotherm plots of Form F of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide.

DVS isotherms plots are reported in FIG. 56, wherein the red line depicts the first sorption phase, the blue line depicts the first desorption phase, the green line depicts the second sorption phase and the pink line depicts the second desorption phase.

The DVS analyses show that Form F is stable at up to approximately 50% RH and that at 90% RH, the sample showed a weight increase that is greater than 50% w/w. After this event the sample releases and takes water reversibly.

Stability of Form F

The sample becomes a viscous liquid after a day at 25° C. and 60% RH and after a day at 60° C. and 75% RH.

Hygroscopicity of Form F

The hygroscopicity was calculated using the following equation:

% Weight Change$=[(W2-W1)/W1]*100$ wherein,
W1 is weight of sample at the start of the experiment; and
W2 is weight of sample at 25° C. and 80% RH in the first absorption cycle.

Obtained results show that the sample is very hygroscopic, with a mass increase that is greater than 15%, and becomes a viscous liquid at high humidity.

The analytical methods used for the product assessment are performed as described below.

Analytical methods

HPLC method

Column: ZORBAX Eclipse XDB-C18 (150×4.6 mm, 5 μm); column temperature 25° C.

Mobile phase: A: Sodium dihydrogen orthophosphate dihydrate 0.05 M; B: Acetonitrile Gradient:

| Time (min) | % A | % B |
|------------|-----|-----|
| 0 | 95 | 5 |
| 10 | 5 | 95 |
| 10.2 | 95 | 5 |
| 12 | 95 | 5 |

Flow: 1.0 mL/min
Detector: UV DAD@220 nm

The obtained crystalline products of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide Form A, B, C, D, E and F have an HPLC purity of at least 98%, preferably at least 99%, preferably at least 99.5%, preferably at least 99.6%, preferably at least 99.7%, preferably at least 99.8%, preferably at least 99.9%.

NMR

The samples for NMR analysis were prepared by complete dissolution of an appropriate amount of material in approximately 0.75 ml of NMR solvent (DMSO-d6)

1H NMR spectra were recorded at 25° C. using an either a Varian INOVA 400 MHz NMR Spectrometer equipped with a Varian ATB probe.

Variable number of scans (16-256) was applied, using standard acquisition parameters. The pre-acquisition delay was set to 10 sec whenever NMR quantification was carried out. Appropriate phasing and baseline corrections were applied in processing the spectra.

XRPD

The XRPD spectra were collected in transmission mode on an analytical X'pert Pro instrument with X'celerator detector using a standard Aptuit method. The data were evaluated using the HighScore Plus software. The instrumental parameters used are listed below.

| Instrumental parameter | Value |
|------------------------|-------|
| 2-theta range | 2-45 |
| Step size [°2-theta] | 0.0170 |
| Time per step [sec] | 60.7285 sec |
| Wavelength [nm] | 0.154060 (Cu K-Alpha1) |
| Rotation [Yes/No] | Yes |
| Slits divergence/ antiscatter. | Incident Mask fixed 10 mm; Divergence slits ½, Antiscat. slits ½ on incident beam; 1/32 on diffracted |
| X-ray Mirror | Inc. Beam Cu W/Si focusing MPD, Acceptance Angle 0.8°, Length 55.3 mm |
| Temperature | Room temperature |
| Humidity values [% RH] | Ambient |

-continued

| Instrumental parameter | Value |
|---|---|
| Fixed Slits | 0.02 rad fixed Soller slits on incident and diffracted beam |
| Monochromator | None |
| Detector type | X'celerator (active length 2.122 2theta degree), scanning mode |
| Sample holder | Transmission sample holder. Use Insert to keep thickness at 1 mm, 5 mm diameter |
| Configuration | Transmission |
| Generator voltage/current | 40 KV/40 mA |

Optical Microscopy

Optical microscopy analyses were run on the Leica DM microscope equipped with a double polarizer and digital camera. The method parameters are listed below.

| | Value |
|---|---|
| Polarized light [Y/N] | Yes |
| Magnification [eyepiece] | 10x |
| Objective | Typically 5x, 10x, 20x, 40x |
| Filter slider | Use the best filter to optimize the image |

TGA and DSC

The TGA analyses were run on a TA Q5000 instrument or on Mettler Toledo Star System (Form F analysis). The DSC analyses were run on the TA Q2000 MDSC or on the DSC 200 F3 Maia (Form F analysis) instruments. DSC and TGA method details are listed below:

| Instrumental parameter | Value |
|---|---|
| | TGA |
| Balance purge gas [mL/min] | 10 |
| Sample purge gas [mL/min] | 25 |
| Gas | Nitrogen |
| Temperature-Time-Rate | Typically from room temperature to 250/350° C. at 10° C./min (TA Q5000 instrument); or to 450° C. at 10° K/min (Mettler Toledo Star System) |
| Typical sample amount [mg] | Usually from 2 mg to 20 mg |
| Pan [Pt/Al] | Hermetically sealed Al (punched) |
| | DSC |
| Instrumental parameter | Value |
| Cooling [ON/OFF] | ON |
| Gas | Nitrogen |
| Temperature-Time-Rate | From 0° C. to ~160° C. Ramp at 10° C./min (TA Q2000 MDSC); or from 25° C. to ~350° C. Ramp at 10° K/min (DSC 200 F3 Maia). |
| Typical sample amount [mg] | Usually from 0.5 mg to 2.5 mg |
| Pan | Not hermetic Al (TA Q2000 MDSC); or hermetically sealed Al ((DSC 200 F3 Maia) |

Raman

Raman analyses were performed with a Keiser Optical Systems RXN1 MicroRaman with Leica Microscope and digital camera

| Instrumental Parameter | Value |
|---|---|
| Probe | N |
| Objective | 50x, 50x LWD, 10x |
| Exposure [sec] | Typically 0.5-1 |

| Instrumental Parameter | Value |
|---|---|
| Laser Power [mW] | 50-400 |
| Autofocus [Y/N] | Typically N |
| Accumulation | Typically 10 |
| Cosmic ray filter [Y/N] | Y |
| Intensity calibration [Y/N] | Y |
| Dark subtract [Y/N] | Y |

FT-IR

FT-IR analyses were performed with a Thermo Nicolet Nexus 470 FT-IR or with a Thermo Nicolet 6700 FT-IR (Form F analyses).

| Instrumental Parameter | Value |
|---|---|
| Accessory | Attenuated Total Reflectance (ATR) - ZnSe Crystal |
| # of scans | 64 |
| Resolution [cm−1] | 4 |
| Gain | Autogain |
| Detector | DTGS KBr |
| Spectral Range [cm−1] | 4000-650 |

Particle Size Distribution

Particle Size Distribution by laser light scattering was performed after developing a wet dispersion method using Malvern Mastersizer 2000 instrument. The method parameters are listed below.

Instrument Malvern Mastersizer 2000
Accessory Hydro2000S+
Parameter Value
Stirring speed 1750 rpm
Dispersant 0.1% w/v Span85/Cyclohexane
Sample Quantity Around 100 mg suspended in 5 mL of dispersant
Calculation Model General Purpose—Irregular
Optical Model Fraunhofer with 1.426 refractive index for the dispersant
Sweeps number 15000 background/15000 sample
Laser Obscuration [%] between 5 and 20% (typically 8-12%)

The experiments were conducted using the following sample preparation:
(i) 100 mg of material were weighted in a 10 ml vial and they were suspended in 5 mL of dispersant;
(ii) once the material was all wetted the suspension was added into the cell and the vial was washed using additional 5 mL of the dispersant;
(iii) the suspension was measured immediately.

EGA

The EGA analysis was carried out on the gas produced during the TGA analysis.

DVS Analyses

Instrument Details
Temperature range: 20-40° C. (standard)
Maximum sample mass: (low/high mass instrument) 1 g/4 g
Mass change: +/−150 mg
Stability (24 hours @25° C. and 0% RH) <5 μg
Mass resolution: +/−0.1 μg
Humidity Range: 0-98% RH
RH Accuracy: +/−1% RH
Temperature stability: +/−0.1° C.
Typical gas flow rate: 100/200 sccm
Sample chamber: 40 mm wide×50 mm deep×50 mm high Reservoir volume: 100 ml reservoir capacity
Heating system: Peltier+Cartridges The kinetic moisture sorption measurement was performed at 25° C. and in a RH % range described in the following:

From 40% RH to 90% RH
Form 90% RH to 0% RH
From 0% RH to 90% RH
From 90% RH to 0% RH The experiment is performed on 10-15 mg of sample and the equilibrium criterion is set as dm/dt<0.002% w/w in 10 min with a maximum step time of 240 min.

Stability Tests

The sample was positioned on the sample holder and stored in the following conditions:

25° C. and 60% RH for 7 days
60° C. and 75% RH for 3 days

The samples were analyzed after the test by XRPD.

Hygroscopicity

The hygroscopicity of the sample was determined using the method reported in the academic article "Efficient throughput method for hygroscopicity classification of an active and inactive pharmaceutical ingredients by water vapor sorption analysis" V. Murikipudi et al., Pharmaceutical Development and Technology, 2013, 18(2): 348-358.

The hygroscopicity was calculated using the following equation:

$$\% \text{ Weight Change} = [(W2-W1)/W1]*100; \text{ wherein}$$

W1 is a weight of sample at the start of the experiment; and
W2 is a weight of sample at 25° C. and 80% RH in the first absorption cycle.

Classification Criteria

Non hygroscopic: increase in mass is less than 0.2%;
Slightly hygroscopic: increase in mass is less than 2% and equal to or greater than (0.2%;
Hygroscopic: increase in mass is less than 15% and equal to or greater than 2%;
Very Hygroscopic: increase in mass is equal to or greater than 15%; and
Deliquescent: sufficient water is absorbed to form a liquid.

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A crystalline compound of formula (I):

Formula (I)

wherein the compound has an XRPD spectrum comprising four or more peaks selected from peaks with 2θ angles of: 8.82, 12.07, 14.43, 14.92, 16.26, 18.25, 19.06, 19.78, 20.82 and 23.51±0.1 degrees 2θ; or four or more peaks selected from peaks with 2θ angles of: 9.33, 10.73, 14.85, 15.29, 15.77, 16.16, 18.60, 20.12, 21.00 and 23.22±0.1 degrees 2θ; or four or more peaks selected from peaks with 2θ angles of: 6.7824, 15.4567, 16.3961, 17.1082, 20.0651, 20.6373, 23.2376, 23.6811, 26.1802 and 32.4753±0.05 degrees 2θ; or four or more peaks selected from peaks with 2θ angles of: 6.8269, 15.0475, 15.6848, 16.4735, 17.1773, 18.4488, 20.6999, 23.3436, 23.8843 and 25.3818±0.05 degrees 2θ.

2. A crystalline compound according to claim 1, with an XRPD spectrum substantially as shown in FIG. 1.

3. A crystalline compound according to claim 1, the compound having a Thermo Gravimetric Analysis (TGA) curve showing an endothermic event at about 163° C.±2° C.

4. A crystalline compound according to claim 1, the compound having a Differential Scanning calorimetry (DSC) curve showing an endothermic event at about 163° C.±2° C.

5. A crystalline compound of formula (I):

Formula (I)

wherein the compound has an XRPD spectrum comprising four or more peaks selected from peaks with 2θ angles of: 9.37, 10.34, 12.59, 13.17, 15.00, 15.63, 18.51, 19.10, 20.79 and 23.93±0.10 degrees 2θ.

6. A crystalline compound according to claim 5, the compound having an XRPD spectrum substantially as shown in FIG. 2.

7. A crystalline compound according to claim 5, the compound having a Thermo Gravimetric Analysis (TGA) curve showing an endothermic event at about 155° C.±2° C.

8. A crystalline compound according to claim 5, the compound having a Differential Scanning calorimetry (DSC) curve showing an endothermic event at about 180° C.±2° C.

9. A crystalline compound of formula (I):

Formula (I)

wherein the compound has an XRPD spectrum comprising four or more peaks selected from peaks with 2θ angles of: 12.7398, 15.3615, 15.9547, 16.4290, 18.1207, 20.4870, 22.8548, 23.2204, 27.0457, 27.6934 and 32.4785±0.05 degrees 2θ.

10. A crystalline compound according to claim 9, the compound having an XRPD spectrum substantially as shown in FIG. 29.

11. A crystalline compound according to claim 9, the compound having a Thermo Gravimetric Analysis (TGA) curve showing an endothermic event at about 160° C.

12. A crystalline compound according to claim 9, the compound having a DSC profile showing an exothermic peak at approximately 184° C.

13. A process for preparing a crystalline compound, the process comprising the steps of:
forming a formulation by dissolving or suspending an amorphous compound of formula (I) in a solvent consisting of N,N-dimethylformamide; and
crystallizing the compound of formula (I) from the formulation;

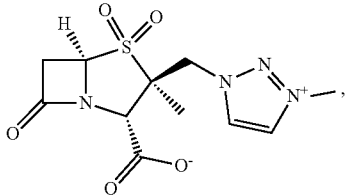

Formula (I)

wherein the compound has an XRPD spectrum comprising four or more peaks selected from peaks with 2θ angles of:

12.73±0.05 degrees 2θ, 15.36±0.05 degrees 2θ, 15.95±0.05 degrees 2θ, 16.42±0.05 degrees 2θ, 18.12±0.05 degrees 2θ, 20.48±0.05 degrees 2θ, 22.85±0.05 degrees 2θ, 23.22±0.05 degrees 2θ, 27.04±0.05 degrees 2θ, 27.69±0.05 degrees 2θ and 32.47±0.05 degrees 2θ.

14. A method of treating a bacterial infection comprising administering to a patient in need thereof a therapeutically effective amount of a pharmaceutical composition comprising a crystalline compound according to claim 9.

15. A method of treating a bacterial infection comprising co-administering to a patient in need thereof a therapeutically effective amount of a pharmaceutical composition comprising a crystalline compound according to claim 9 and a therapeutically effective amount of an antiobiotic.

16. The process according to claim 13, wherein crystals are allowed to form from the solution for more than four hours before separation of crystals from the solvent.

17. The process according to claim 13, wherein crystals are allowed to form from the solution for at least six hours before separation of crystals frorm the solvent.

18. The process according to claim 17, wherein the temperature of the solution is reduced while the crystals are allowed to form.

* * * * *